US012810584B2

(12) United States Patent
Sakamoto et al.

(10) Patent No.: US 12,810,584 B2
(45) Date of Patent: Nov. 24, 2026

(54) INFORMATION PROCESSING DEVICE, INFORMATION PROCESSING METHOD, AND PROGRAM

(71) Applicant: TERUMO KABUSHIKI KAISHA, Tokyo (JP)

(72) Inventors: Yasukazu Sakamoto, Hiratsuka (JP); Katsuhiko Shimizu, Fujinomiya (JP); Hiroyuki Ishihara, Tokyo (JP); Shunsuke Yoshizawa, Ebina (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 304 days.

(21) Appl. No.: 18/474,476

(22) Filed: Sep. 26, 2023

(65) Prior Publication Data

US 2024/0013514 A1 Jan. 11, 2024

Related U.S. Application Data

(63) Continuation of application No. PCT/JP2022/010473, filed on Mar. 10, 2022.

(30) Foreign Application Priority Data

Mar. 30, 2021 (JP) ................................ 2021-058296

(51) Int. Cl.

*G06V 10/764* (2022.01)
*A61B 8/00* (2006.01)

(Continued)

(52) U.S. Cl.

CPC .............. *G06V 10/764* (2022.01); *A61B 8/12* (2013.01); *A61B 8/4494* (2013.01); *G06V 10/267* (2022.01); *G06V 2201/03* (2022.01)

(58) Field of Classification Search

CPC ...... G06V 10/764; G06V 20/70; G06V 40/14; A61B 8/12; A61B 8/0891; A61B 1/00009

See application file for complete search history.

(56) References Cited

U.S. PATENT DOCUMENTS

| | | | | |
|---|---|---|---|---|
| 10,631,737 B2 * | 4/2020 | Lavi | .................. | A61B 5/02007 |
| 2009/0148024 A1 * | 6/2009 | Park | ........................ | G06T 7/162 382/134 |

(Continued)

FOREIGN PATENT DOCUMENTS

| | | |
|---|---|---|
| JP | 2013543786 A | 12/2013 |
| JP | 2015173820 A | 10/2015 |

(Continued)

OTHER PUBLICATIONS

M. Alberti et al., "Automatic Bifurcation Detection in Coronary IVUS Sequences," in IEEE Transactions on Biomedical Engineering, vol. 59, No. 4, pp. 1022-1031, Apr. 2012, doi: 10.1109/TBME.2011.2181372. (Year: 2012).*

(Continued)

*Primary Examiner* — Chan S Park
*Assistant Examiner* — Chandhana Pedapati
(74) *Attorney, Agent, or Firm* — Buchanan Ingersoll & Rooney PC

(57) ABSTRACT

An information processing device that includes a classification image data acquisition unit configured to acquire a plurality of classification image data classified into a plurality of regions including a first intraluminal region into which the image acquisition catheter for a three-dimensional scan is inserted and a second intraluminal region into which the image acquisition catheter is not inserted; a merging determination unit configured to determine whether the second intraluminal region in a first catheter image merges with the first intraluminal region in a second catheter image acquired at a different axial position; and an image output (Continued)

unit configured to output a region image including the first intraluminal region based on the plurality of classification image data, and outputs, only the second intraluminal region that is determined to merge by the merging determination unit, together with the first intraluminal region as the region image.

18 Claims, 21 Drawing Sheets

(51) Int. Cl.
*A61B 8/12* (2006.01)
*G06V 10/26* (2022.01)

(56) References Cited

U.S. PATENT DOCUMENTS

2012/0130243 A1 5/2012 Balocco et al.
2013/0225943 A1* 8/2013 Holsing .................... G06T 7/12 600/409
2014/0270429 A1* 9/2014 Nair .......................... G06T 7/11 382/128
2015/0257850 A1 9/2015 Sakamoto
2017/0262733 A1* 9/2017 Gulsun ................ G06V 10/454
2017/0301084 A1 10/2017 Gopinath
2019/0021694 A1 1/2019 Sakaguchi
2019/0125173 A1* 5/2019 Lee ....................... G06T 7/0012
2020/0167923 A1 5/2020 Gopinath
2020/0226422 A1 7/2020 Li et al.
2023/0230231 A1* 7/2023 Tu .......................... G06N 3/045 382/130

FOREIGN PATENT DOCUMENTS

JP 2019513453 A 5/2019
WO WO-2016104288 A1 * 6/2016 ............... A61B 1/00
WO 2017164071 A1 9/2017

OTHER PUBLICATIONS

Extended European Search Report issued on Jun. 28, 2024, in corresponding European Patent Application No. 22779915.2. (11 pages).
Zhao Mengliu, “Encoding Anatomical Tree Priors for Tubular Structure Extraction for Medical Images Analysis”, Computing Science Theses, (Apr. 2, 2020), pp. 1-157, XP093174050, Retrieved from the Internet: URL:https://summit.sfu.ca/item/2003.
International Search Report (PCT/ISA/210) with translation and Written Opinion (PCT/ISA/237) mailed on May 31, 2022, by the Japan Patent Office as the International Searching Authority for International Application No. PCT/JP2022/010473. (8 pages).

* cited by examiner

61

| | |
|---|---|
| THREE-DIMENSIONAL SCAN ID | A001 |

| NUMBER | CATHETER IMAGE | CLASSIFICATION IMAGE DATA | NON-CHANGED CLASSIFICATION IMAGE DATA |
|---|---|---|---|
| 1 |  |  | |
| ⋮ | ⋮ | ⋮ | |
| X1 |  |  |  |
| ⋮ | ⋮ | ⋮ | |
| X2 |  |  | |
| ⋮ | ⋮ | ⋮ | |
| X3 |  |  |  |
| ⋮ | ⋮ | ⋮ | |
| X4 |  |  | |
| ⋮ | ⋮ | ⋮ | |

INFORMATION PROCESSING DEVICE, INFORMATION PROCESSING METHOD, AND PROGRAM

CROSS-REFERENCES TO RELATED APPLICATIONS

This application is a continuation of International Application No. PCT/JP2022/010473 filed on Mar. 10, 2022, which claims priority to Japanese Application No. 2021-058296 filed on Mar. 30, 2021, the entire content of both of which is incorporated herein by reference.

TECHNOLOGICAL FIELD

The present disclosure generally relates to an information processing device, an information processing method, and a program.

BACKGROUND DISCUSSION

A catheter system is used in which an image acquisition catheter is inserted into a lumen organ such as a blood vessel to acquire an image (International Patent Application Publication No. WO2017/164071).

However, in a site having a complicated structure in which a merging portion, a bifurcated portion, and the like of a lumen organ are present, it may be difficult for a user to quickly understand an image acquired by an image acquisition catheter.

SUMMARY

An information processing device or the like is disclosed that assists understanding of an image acquired by an image acquisition catheter.

An information processing device includes: a classification image data acquisition unit configured to acquire a plurality of classification image data, the plurality of classification image data being generated based on a plurality of catheter images acquired using an image acquisition catheter that acquires an image while moving in an axial direction on a scan plane, the plurality of classification image data being classified into a plurality of regions including a first intraluminal region into which the image acquisition catheter is inserted and a second intraluminal region into which the image acquisition catheter is not inserted; a merging determination unit configured to determine whether the second intraluminal region in a first catheter image of the plurality of catheter images merges with the first intraluminal region in a second catheter image acquired at an axial position different from an axial position of the first catheter image; and an image output unit configured to output a region image including the first intraluminal region based on the plurality of classification image data. The image output unit outputs, of the second intraluminal region, only the second intraluminal region in the first catheter image that is determined to merge by the merging determination unit, together with the first intraluminal region as the region image.

In one aspect, it is possible to provide the information processing device or the like that assists understanding of an image acquired by the image acquisition catheter.

In another aspect, an information processing method executed by a computer, the information processing method comprising: acquiring a plurality of classification image data, the plurality of classification image data being generated based on a plurality of catheter images acquired using an image acquisition catheter that acquires an image while moving in an axial direction on a scan plane, the plurality of classification image data being classified into a plurality of regions including a first intraluminal region into which the image acquisition catheter is inserted and a second intraluminal region into which the image acquisition catheter is not inserted; determining whether the second intraluminal region in a first catheter image of the plurality of catheter images merges with the first intraluminal region in a second catheter image acquired at an axial position different from an axial position of the first catheter image; and outputting, of the second intraluminal region, only the second intraluminal region in the first catheter image that is determined to merge based on the plurality of classification image data, together with the first intraluminal region as a region image.

In one aspect, a non-transitory computer-readable medium storing a program causing a computer to execute a process comprising: acquiring a plurality of classification image data, the plurality of classification image data being generated based on a plurality of catheter images acquired using an image acquisition catheter that acquires an image while moving in an axial direction on a scan plane, the plurality of classification image data being classified into a plurality of regions including a first intraluminal region into which the image acquisition catheter is inserted and a second intraluminal region into which the image acquisition catheter is not inserted; determining whether the second intraluminal region in a first catheter image of the plurality of catheter images merges with the first intraluminal region in a second catheter image acquired at an axial position different from an axial position of the first catheter image; and outputting, of the second intraluminal region, only the second intraluminal region in the first catheter image that is determined to merge based on the plurality of classification image data, together with the first intraluminal region as a region image.

DETAILED DESCRIPTION

Set forth below with reference to the accompanying drawings is a detailed description of embodiments of an information processing device, an information processing method, and a program.

First Embodiment

Figure 1:
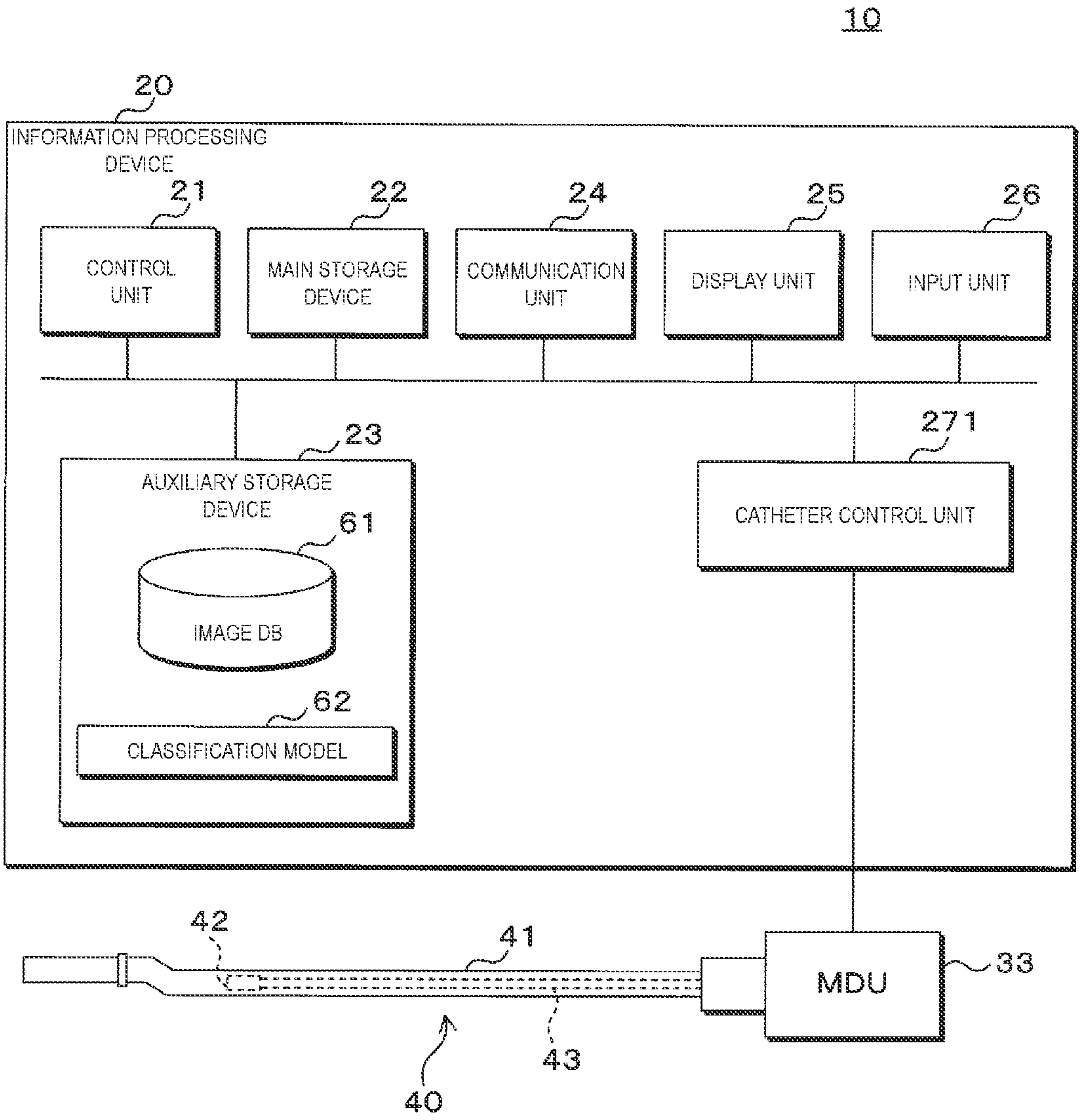
FIG. 1 is a diagram showing a configuration of a catheter system.

FIG. 1 is a diagram showing a configuration of a catheter system 10. The catheter system 10 includes a three-dimensional image acquisition catheter 40, a motor driving unit (MDU) 33, and an information processing device 20.

The three-dimensional image acquisition catheter 40 includes an elongated sheath 41, a sensor 42, and a shaft 43 disposed inside the sheath 41. The sensor 42 can be attached to an end portion of the shaft 43. The three-dimensional image acquisition catheter 40 is connected to the information processing device 20 via the MDU 33.

The sensor 42 can be, for example, an ultrasound transducer that transmits and receives ultrasound, or a transmitting and receiving unit for optical coherence tomography (OCT) that emits near-infrared light and receives reflected light. In the following description, an example will be described in which the three-dimensional image acquisition catheter 40 is an ultrasound catheter used for performing so-called three-dimensional scan in which a plurality of ultrasound tomographic images are continuously generated from an inside of a lumen organ.

The information processing device 20 can include a control unit 21, a main storage device 22, an auxiliary storage device 23, a communication unit 24, a display unit 25, an input unit 26, a catheter control unit 271, and a bus. The control unit 21 can be an arithmetic and control apparatus that executes a program according to the present embodiment. One or a plurality of central processing units (CPUs), graphics processing units (GPUs), multi-core CPUs, or the like can be used as the control unit 21. The control unit 21 is connected to hardware units constituting the information processing device 20 via a bus.

The main storage device 22 can be a storage device such as a static random access memory (SRAM), a dynamic random access memory (DRAM), or a flash memory. Information required during processing of the control unit 21 and a program being executed by the control unit 21 are temporarily stored in the main storage device 22.

The auxiliary storage device 23 is a storage device such as an SRAM, a flash memory, a hard disk, or a magnetic tape. The auxiliary storage device 23 stores an image database (DB) 61, a classification model 62, a program to be executed by the control unit 21, and various types of data necessary for executing the program. The communication unit 24 is an interface for performing communication between the information processing device 20 and a network. The image DB 61 may be stored in an external large-capacity storage device or the like connected to the information processing device 20.

The display unit 25 can be, for example, a liquid crystal display panel or an organic electro luminescence (EL) panel. The input unit 26 can be, for example, a keyboard and a mouse. The input unit 26 may be stacked on the display unit 25 to form a touch panel. The display unit 25 may be a display apparatus connected to the information processing device 20.

The MDU 33 simultaneously advances and retracts while rotating the sensor 42 and the shaft 43. The catheter control unit 271 generates one catheter image 55 (see FIG. 2) for each rotation of the sensor 42. The generated catheter image 55 is a so-called transverse tomographic image centered on the sheath 41 and substantially perpendicular to the sheath 41. In the following description, generating the catheter image 55 by the catheter control unit 271 may be referred to as "capturing the catheter image 55".

The catheter control unit 271 continuously captures a plurality of catheter images 55 substantially perpendicular to the sheath 41 by an operation of rotating the sensor 42 while pulling or pushing the sensor 42 in an axial direction within the sheath 41. The continuously captured catheter images 55 can be used to construct a three-dimensional image.

An advancing and retracting operation of the sensor 42 may be an operation of advancing and retracting the sensor 42 and the shaft 43 inside the sheath 41 or an operation of advancing and retracting the sheath 41, the sensor 42, and the shaft 43 integrally. The advancing and retracting operation may be automatically performed at a predetermined speed by the MDU 33 or may be manually performed by a user. In the following description, a direction in which the sensor 42 advances and retreats, that is, a longitudinal direction of the sheath 41 may be referred to as an axial direction.

In the following description, a case where the sensor 42 and the shaft 43 are automatically pulled toward the MDU 33 at a constant speed while rotating inside the sheath 41 will be described as an example. In the following description, a series of scans performed while the sensor 42 is pulled once is referred to as one three-dimensional scan.

Note that the three-dimensional image acquisition catheter 40 is not limited to a mechanical scanning system that mechanically rotates and advances and retracts. An electronic radial scan three-dimensional image acquisition catheter 40 using a sensor 42 in which a plurality of ultrasound transducers are annularly arranged may be used. A three-dimensional image acquisition catheter 40 that mechanically rotates an electronic linear sensor 42 in which a plurality of ultrasound transducers are linearly arranged may be used.

The information processing device 20 according to the present embodiment can be a dedicated ultrasound diagnostic apparatus, or a personal computer, a tablet, a smartphone, or the like having a function of the ultrasound diagnostic apparatus. In the following description, a case where the control unit 21 performs software processing will be mainly described as an example. Processing described using a flowchart and various trained models may be implemented by dedicated hardware.

Figure 2:
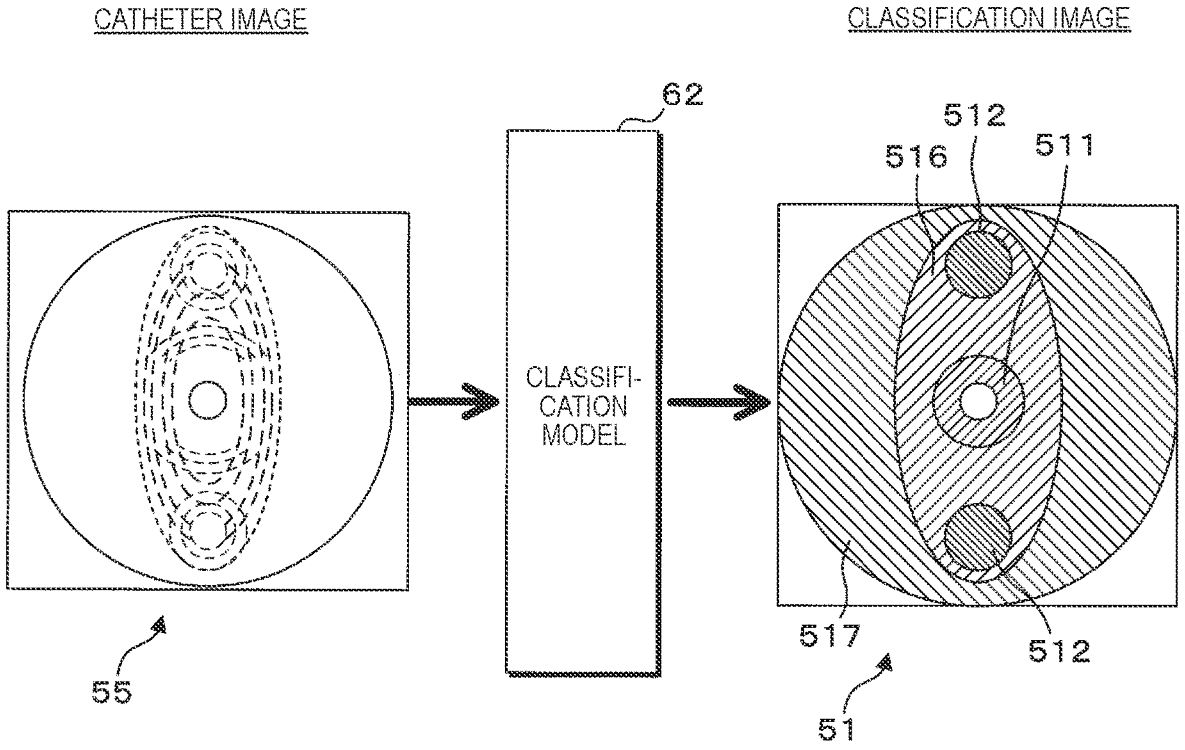
FIG. 2 is a diagram showing a configuration of a classification model.

FIG. 2 is a diagram showing a configuration of the classification model 62. The classification model 62 is a model that receives the catheter image 55 and outputs classification image data. The classification image data is data in which each portion constituting the catheter image 55 is associated with a label classified for each subject depicted in the portion. The portion can be, for example, a pixel. The classified image data can be used to generate the classification image 51 in which the catheter image 55 is painted for each subject depicted.

In the following description, the classification image 51 is used for convenience in order to describe processing performed by the catheter system 10 of the present embodiment. However, the control unit 21 does not need to actually generate the classification image 51 or display the classification image 51 on the display unit 25. The control unit 21 performs following processing by using the classification image data output from the classification model 62 as it is.

A specific example will be described. The classification model 62 classifies pixels constituting the input catheter image 55 into, for example, a first intraluminal region 511, second intraluminal regions 512, a biological tissue region 516, and a non-intraluminal region 517, and outputs classification image data in which positions of pixels are associated with labels indicating classification results.

The first intraluminal region 511 indicates a lumen of a lumen organ into which the three-dimensional image acquisition catheter 40 is inserted. Each of the second intraluminal regions 512 indicates a lumen of a lumen organ into which the three-dimensional image acquisition catheter 40 is not inserted. The biological tissue region 516 indicates a region in which a lumen organ wall such as a blood vessel wall, a cardiac wall, or a gastrointestinal tract wall constituting a lumen organ is combined with a muscle, a nerve, fat, or the like adjacent to or close to the lumen organ.

The non-intraluminal region 517 indicates a region that is not classified into any of the first intraluminal region 511, the second intraluminal region 512, and the biological tissue region 516. For example, when the lumen organ into which the three-dimensional image acquisition catheter 40 is inserted is a left ventricle, the non-intraluminal region 517 includes a region outside a cardiac region and a region outside a cardiac structure. When a range in which the image acquisition catheter 40 can be depicted is relatively small and a distal wall of a left atrium cannot be depicted sufficiently, an inside of the left atrium is also in the non-intraluminal region 517. Similarly, a lumen of the left ventricle, a pulmonary artery, a pulmonary vein, and an aortic arch is also in the non-intraluminal region 517 when a distal wall cannot be sufficiently depicted. A region in which a sufficiently clear image is not depicted due to an acoustic shadow or attenuation of ultrasound or the like is also in the non-intraluminal region 517.

The classification model 62 may classify a medical instrument region corresponding to a medical instrument used simultaneously with the three-dimensional image acquisition catheter 40 such as a guide wire. The classification model 62 may classify lesion regions such as plaques, calcifications, and tumors. The classification model 62 may classify these lesion regions for each type of lesion.

FIG. 2 schematically shows the catheter image 55 displayed in a so-called XY format and the classification image 51 in which classification image data is displayed in the XY format. The classification model 62 may receive an input of the catheter image 55 in a so-called RT format, which is formed by arranging scanning line data formed by the sensor 42 transmitting and receiving ultrasound in parallel in order of scanning angle, and output classification image data. Since a conversion method from the RT format to the XY format is known, description of the conversion method is omitted. Since the catheter image 55 is not affected by interpolation processing or the like when the catheter image 55 is converted from the RT format to the XY format, more appropriate classification image data is generated.

The classification model 62 can be, for example, a trained model for performing semantic segmentation on the catheter image 55. The trained model for performing the semantic segmentation can be generated by machine learning using labeled data obtained by combining the catheter image 55 and the classification image 51 in which each portion of the catheter image 55 is depicted by a specialist for each subject.

The classification model 62 may be a combination of image processing such as edge detection and rule-based classification processing. The classification model 62 may be a combination of a trained model and rule-based classification processing.

FIGS. 3 to 9 are diagrams showing an operation of the catheter system 10. In FIGS. 3 to 10, a case in which a three-dimensional scan is performed at a site in which lumens 58 of a lumen organ, which are lumens of two lumen organs, are substantially parallel will be described as an example. The three-dimensional image acquisition catheter 40 can be inserted from a right side in FIG. 3 into a first lumen 581, which is one lumen 58 of a lumen organ. A merging lumen 585, which has a closed bag shape (i.e., a protruding outward shape) except for a portion continuous with the first lumen 581, communicates with the first lumen 581 at a central portion in a longitudinal direction of the first lumen 581 shown in FIG. 3. A second lumen 582, which is the other lumen 58 of the lumen organ, does not communicate with the first lumen 581.

Figure 3:
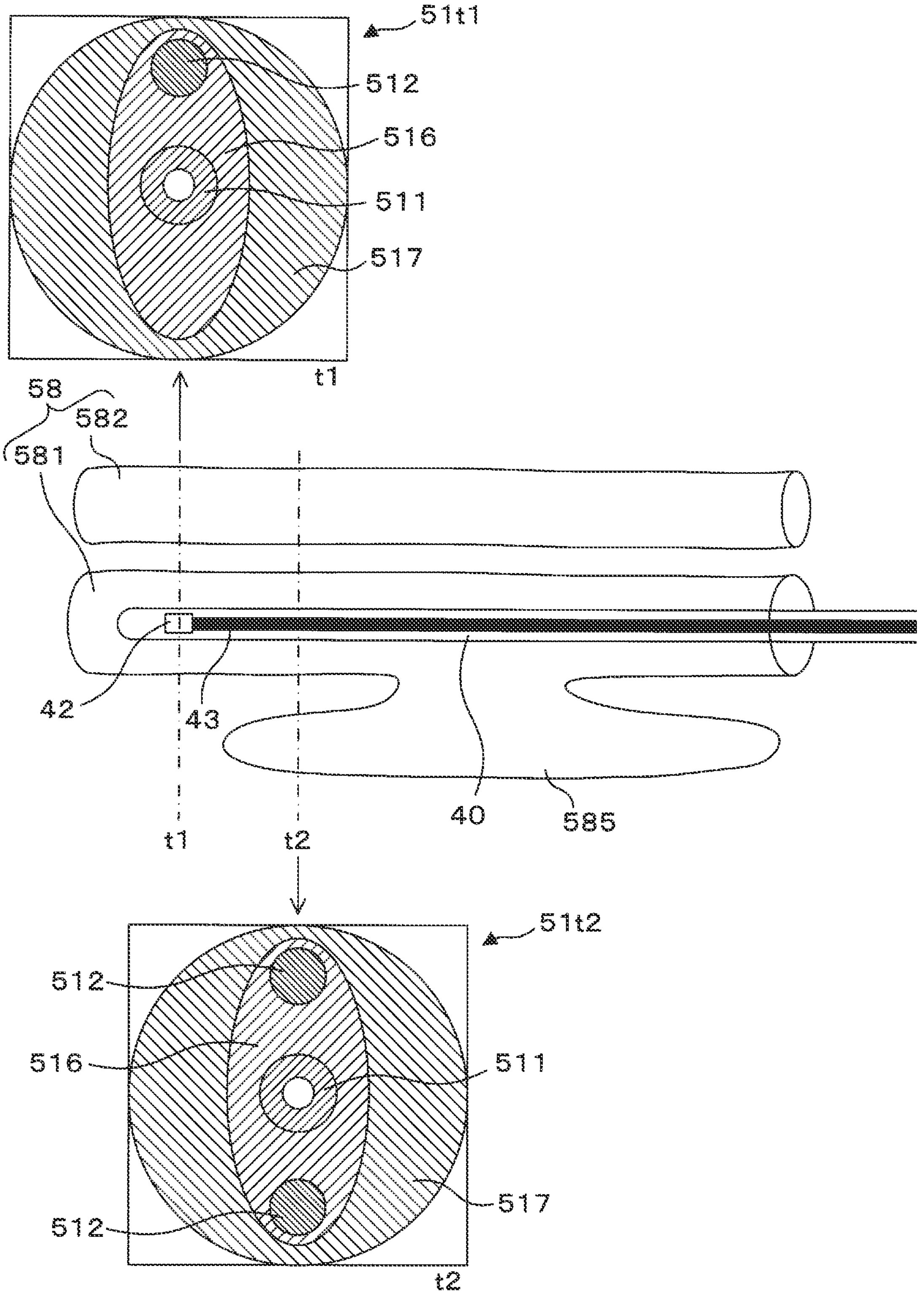
FIG. 3 is a diagram showing an operation of the catheter system.

FIG. 3 shows a position of the sensor 42 at a time t1 that is a start time of the three-dimensional scan. The control unit 21 causes the catheter control unit 271 to start the three-dimensional scan. The catheter control unit 271 captures the catheter image 55 while moving the sensor 42 rightward in FIG. 3. The control unit 21 generates classification image data based on the catheter image 55. For convenience of description, the classification image 51 that can be generated using the classification image data is shown in the drawing. As described above, in processing of the present embodiment, the control unit 21 does not need to generate or display the classification image 51 based on the classification image data.

In the following description, the classification image data generated based on the catheter image 55 captured at a time tx may be referred to as classification image data tx at the time tx. Similarly, the classification image 51 that can be generated using the classification image data tx may be referred to as a classification image 51*tx* at the time tx.

FIG. 3 shows a classification image 51*t*1 at the time t1 and a classification image 51*t*2 at a time t2. In a lower right side of each classification image 51, a time when the catheter image 55 is captured is shown. The classification image 51*t*1 at the time t1 includes the first intraluminal region 511 and the second intraluminal region 512 displayed above the first intraluminal region 511. In the classification image 51*t*2 at the time t2, the second intraluminal region 512 is added on a lower side of the first intraluminal region 511.

Figure 4:
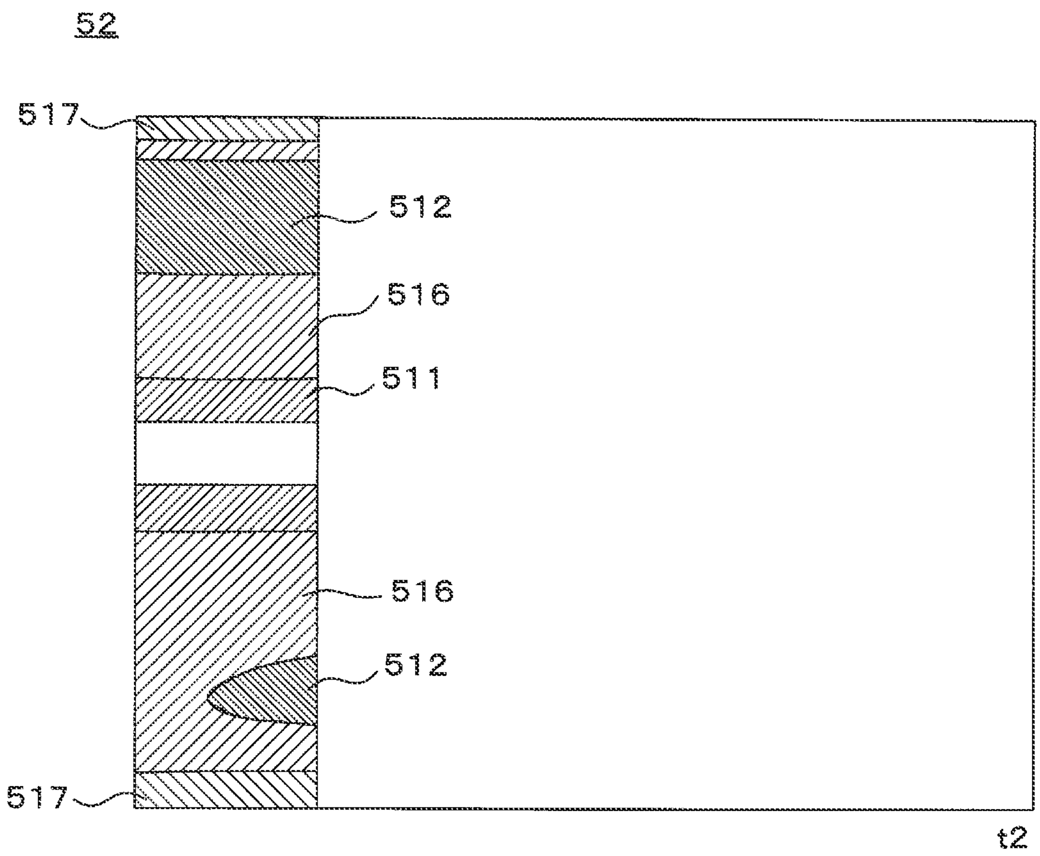
FIG. 4 is a diagram showing an operation of the catheter system.

FIG. 4 shows a linear classification image 52 at the time t2. The linear classification image 52 is an image showing classification of a subject on a so-called linear scan plane along the longitudinal direction of the sheath 41. The linear scan plane includes a central axis of the sheath 41 and is substantially perpendicular to the catheter image 55. Since a method for generating the linear classification image 52 based on a plurality of radial classification images 51 is known, description thereof is omitted.

The linear classification image 52 is also shown for convenience of description. In the processing of the present embodiment, the control unit 21 does not need to generate or display the linear classification image 52. When the linear classification image 52 is temporarily displayed on the display unit 25, the control unit 21 can generate the linear classification image 52 based on a plurality of classification image data without generating the classification image 51.

Figure 5:
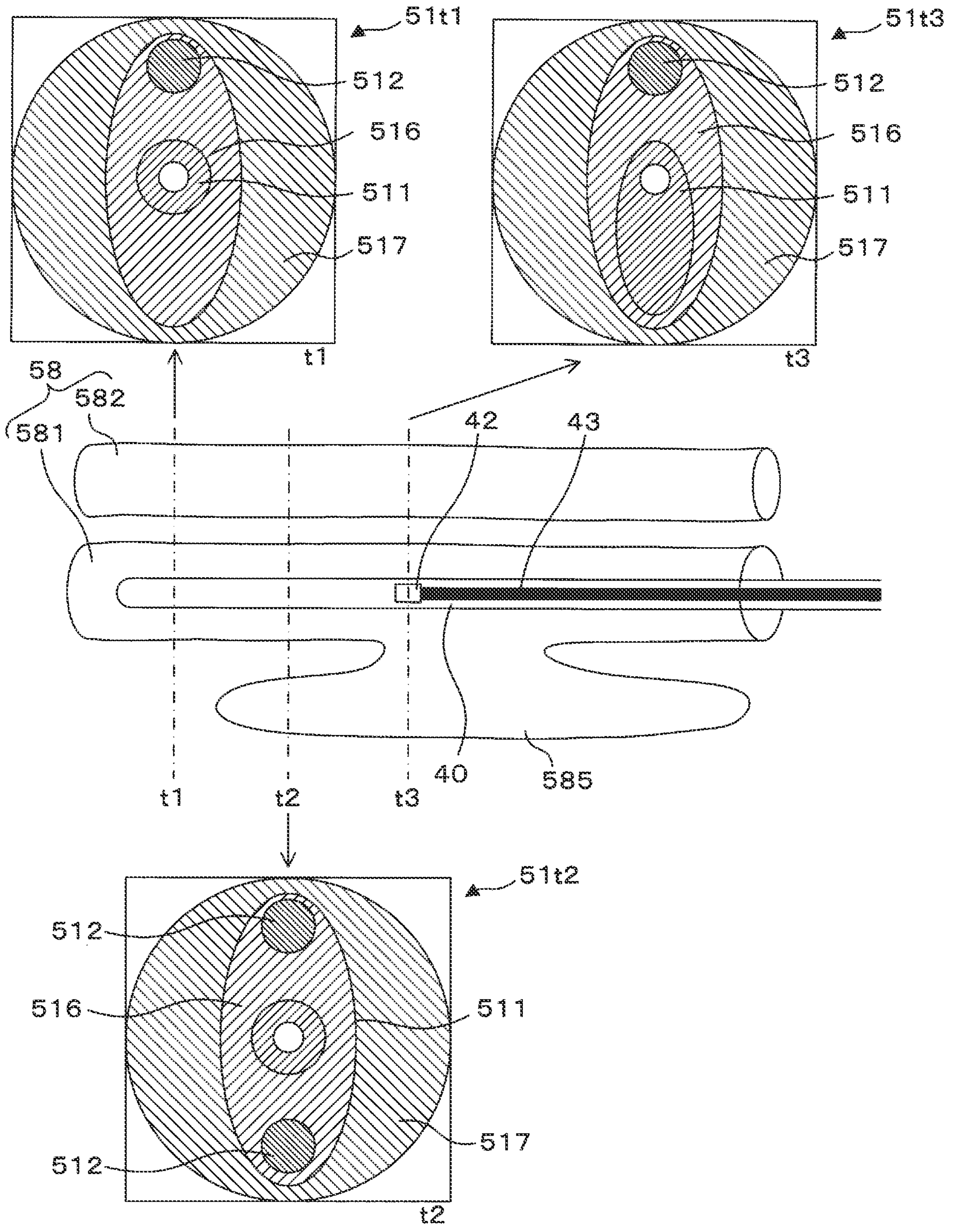
FIG. 5 is a diagram showing an operation of the catheter system.

In FIG. 5, the sensor 42 reaches a merging part of the first lumen 581 and the merging lumen 585. In a classification image 51*t*3 at a time t3, a location of the second intraluminal region 512 on the lower side in the classification image 51*t*2 at the time t2 is changed to the first intraluminal region 511, and the first intraluminal region 511 has a shape elongated downward.

When there is a region changed from the second intraluminal region 512 to the first intraluminal region 511 in the classification image data generated based on adjacent catheter images 55, the control unit 21 determines that the second intraluminal region 512 merges with the first intraluminal region 511. The control unit 21 goes back to the classification image data generated in the past and changes the second intraluminal region 512 determined to merge to the first intraluminal region 511.

Figure 6:
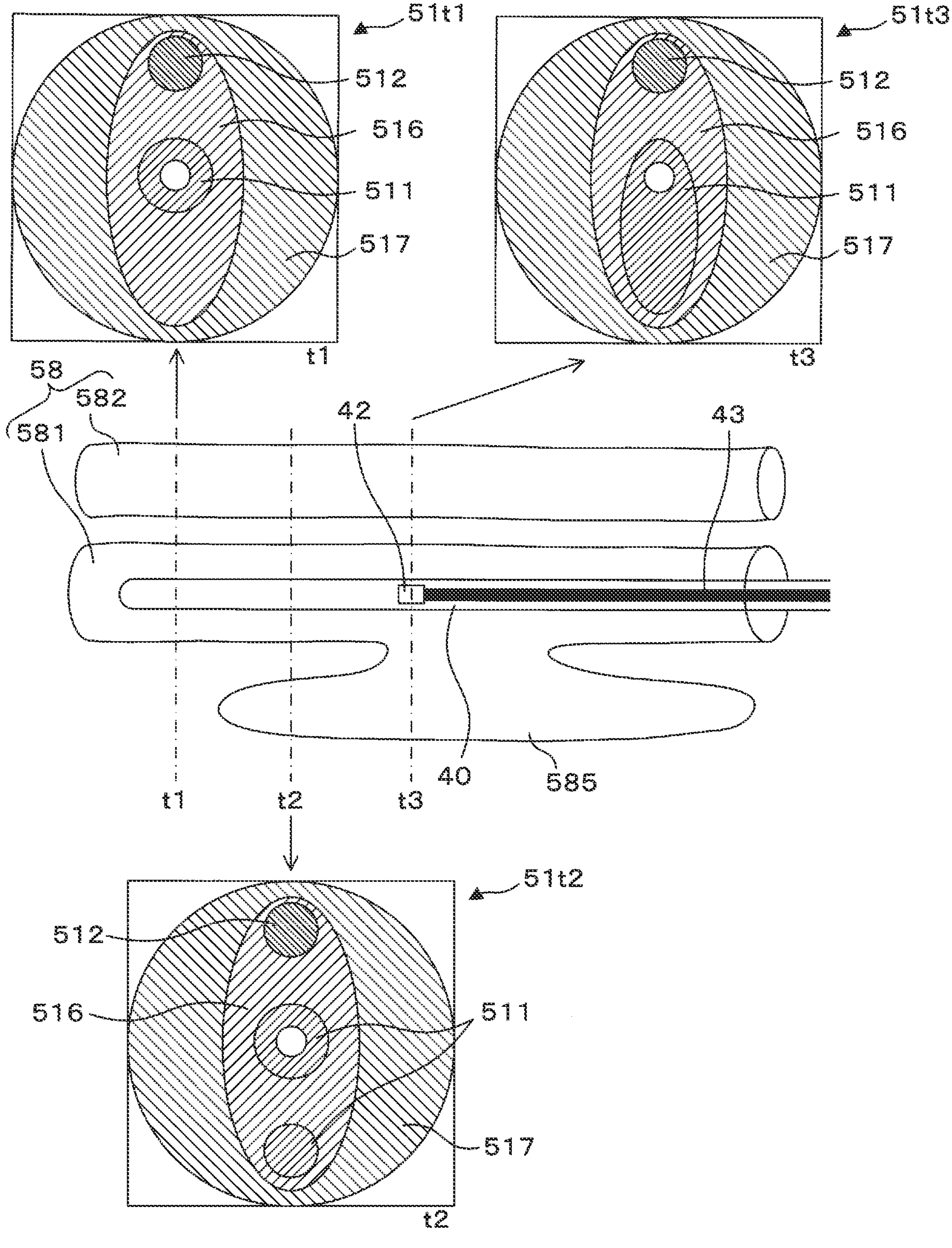
FIG. 6 is a diagram showing an operation of the catheter system.

FIG. 6 shows a state after the control unit 21 changes the classification. In the classification image 51*t*2 at the time t2, the region determined to be the second intraluminal region 512 on the lower side in FIG. 5 is changed to the first intraluminal region 511.

Figure 7:
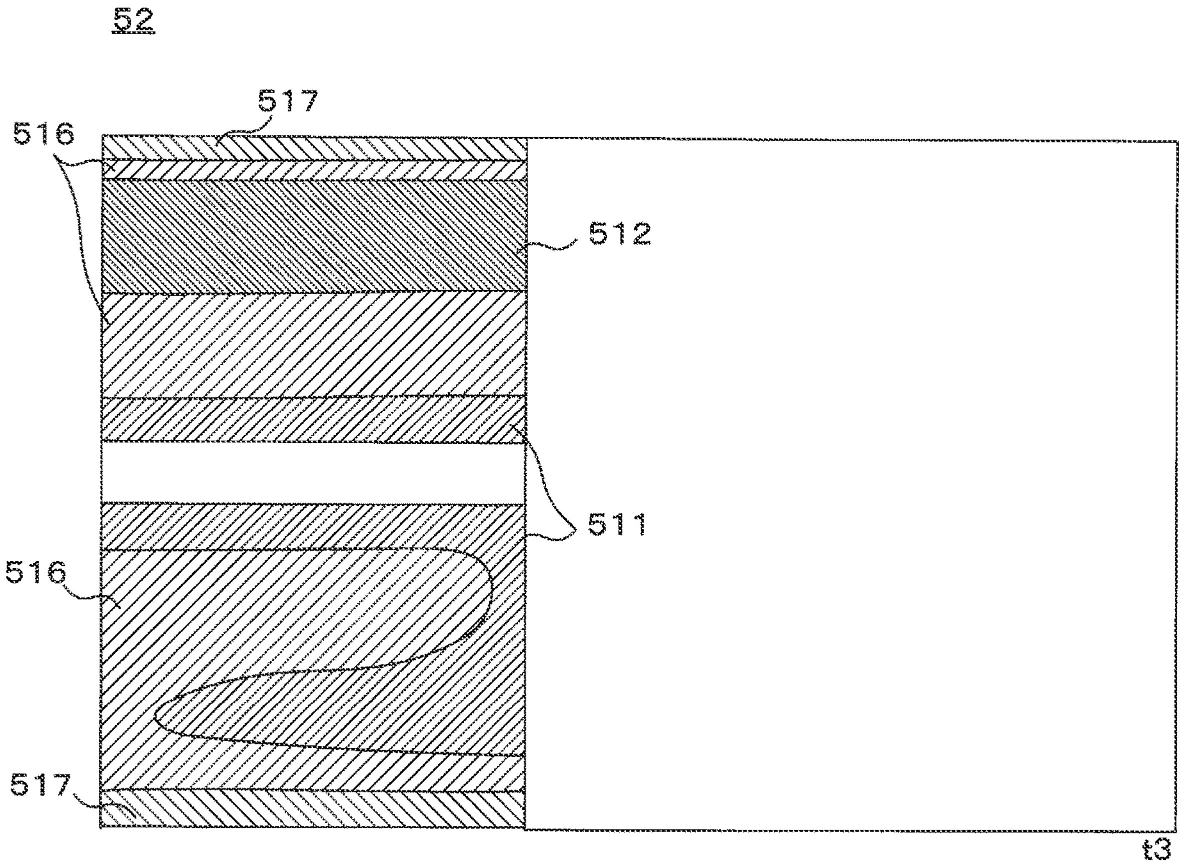
FIG. 7 is a diagram showing an operation of the catheter system.

FIG. 7 shows the linear classification image 52 at the time t3. In FIG. 4, a portion classified as the second intraluminal region 512 is changed to the first intraluminal region 511 in FIG. 7. Therefore, it is clearly expressed that the first intraluminal region 511 and the merging lumen 585 are continuous regions.

Figure 8:
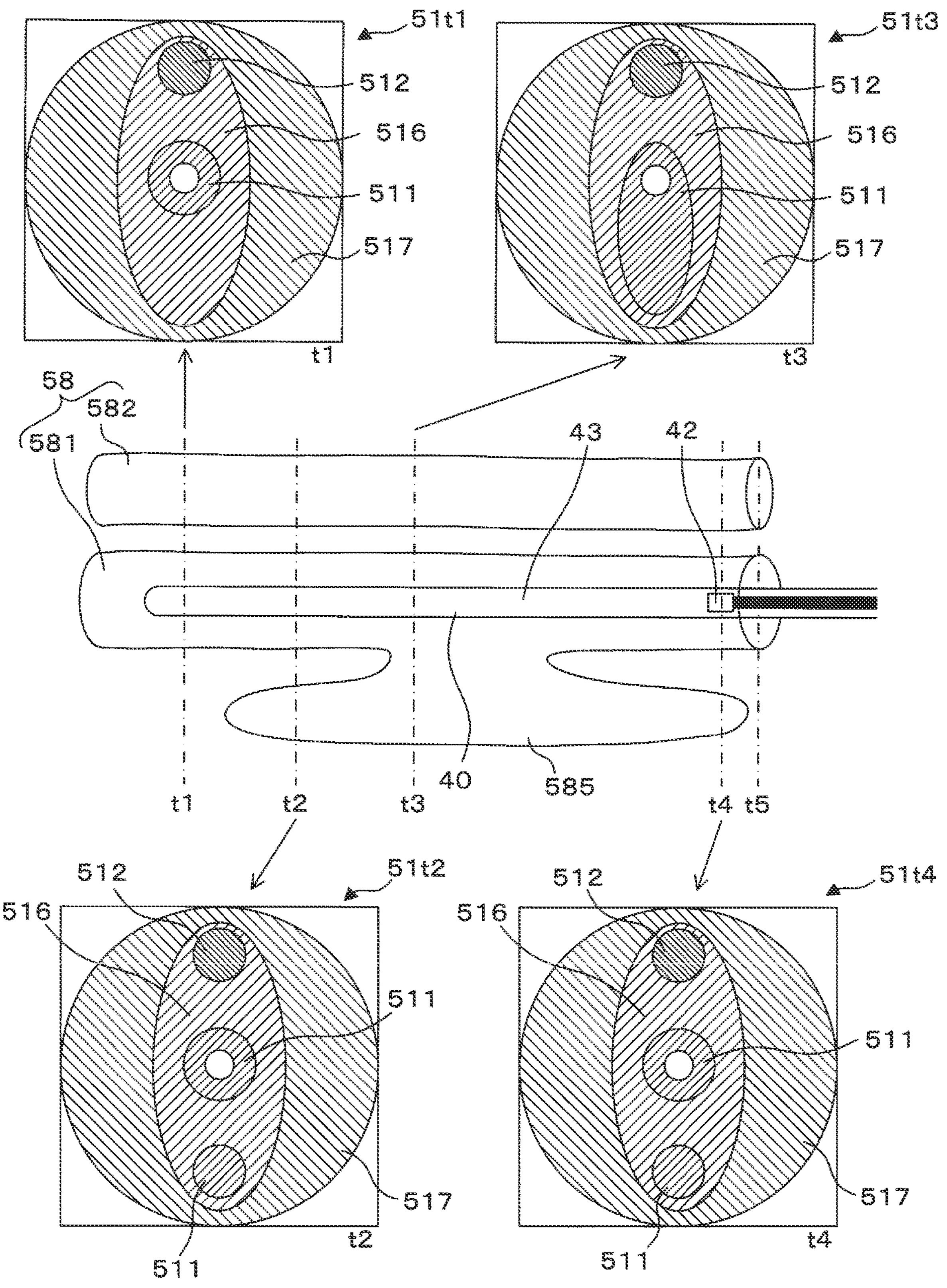
FIG. 8 is a diagram showing an operation of the catheter system.

In FIG. 8, the sensor 42 reaches a position where the first lumen 581 and the merging lumen 585 are separated again. A portion corresponding to the merging lumen 585 is classified as the first intraluminal region 511.

Figure 9:
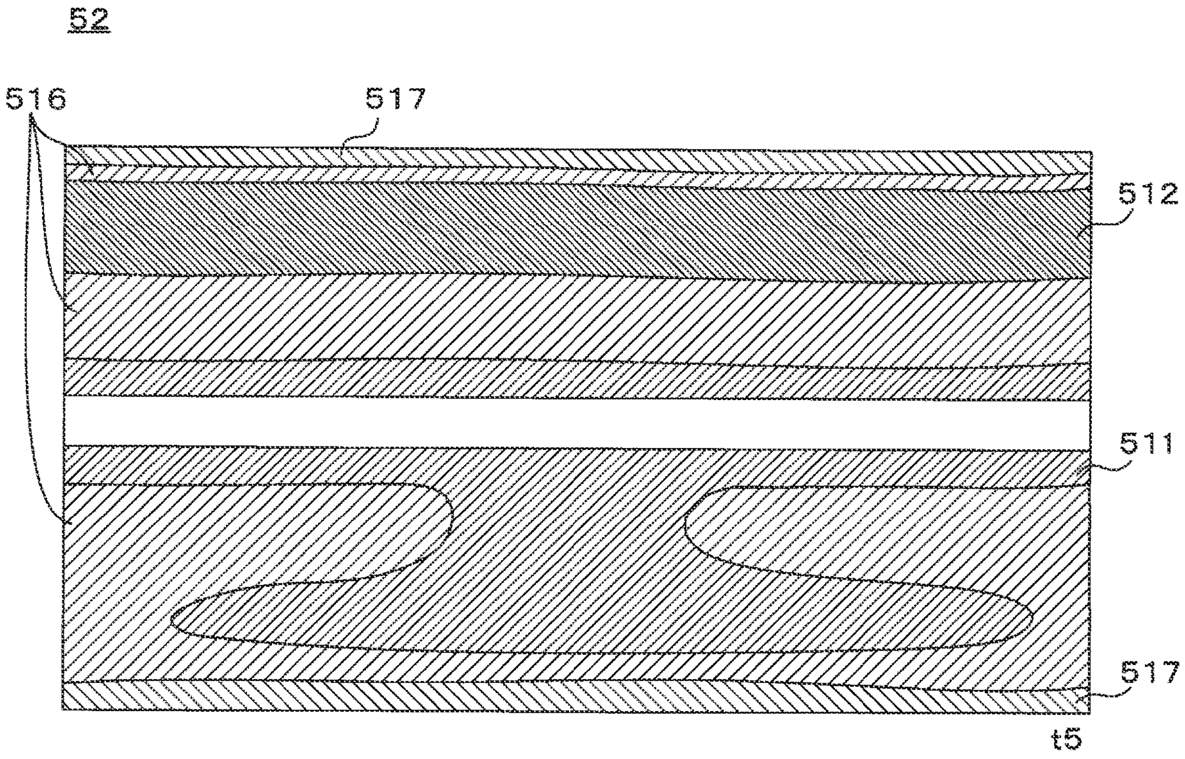
FIG. 9 is a diagram showing an operation of the catheter system.

FIG. 9 shows the linear classification image 52 at a time t5, which is a time when one three-dimensional scan ends. The first intraluminal region 511 and the second intraluminal region 512 extend substantially parallel to each other, and a part of the first intraluminal region 511 protrudes in a bag shape. When the linear classification image 52 shown in FIG. 9 is temporarily displayed on the display unit 25, the user can rather easily understand that the first lumen 581 and the second lumen 582 extend substantially parallel to each other and the bag-shaped merging lumen 585 protrudes from a side surface of the first lumen 581.

Figure 10:
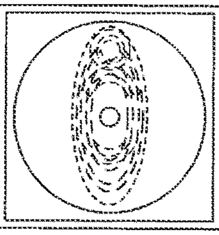
FIG. 10 is a diagram showing a record layout of an image database (DB).
Figure 10:
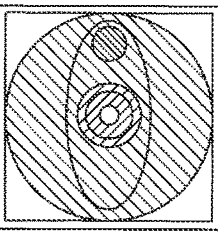
Figure 10:
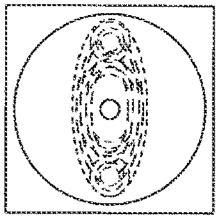
Figure 10:
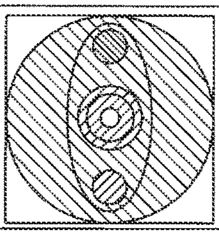
Figure 10:
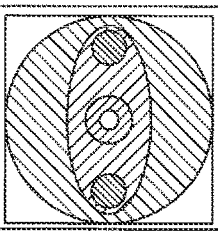
Figure 10:
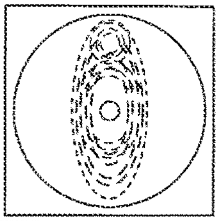
Figure 10:
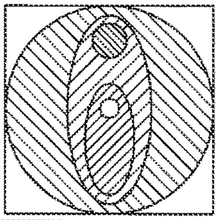
Figure 10:
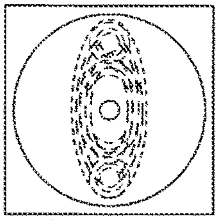
Figure 10:
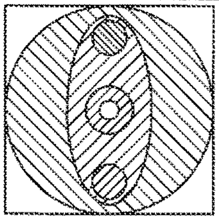
Figure 10:
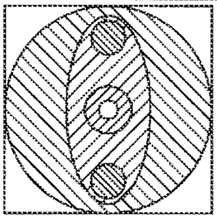
Figure 10:
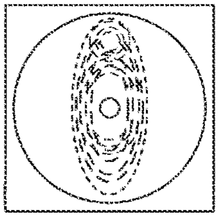
Figure 10:
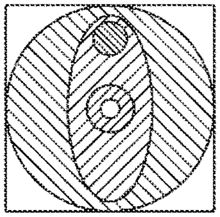

FIG. 10 is a diagram showing a record layout of the image DB 61. The image DB 61 is a database (DB) that records the catheter image 55 and the classification image data in association with each other. The image DB 61 can include a three-dimensional scan ID (identifier) field, a number field, a catheter image field, a classification image data field, and a non-changed classification image data field.

In the three-dimensional scan ID field, a three-dimensional scan ID uniquely assigned to each three-dimensional scan is recorded. In the number field, a number indicating a capturing order is recorded as a consecutive number in each catheter image 55 captured by one three-dimensional scan. In the catheter image field, a file in which the catheter image 55 is recorded or a location of the file in which the catheter image 55 is recorded is recorded.

In the classification image data field, a file in which the classification image data is recorded or a location of the file in which the classification image data is recorded is recorded. As described with reference to FIGS. 5 and 6, in the non-changed classification image data field, non-changed classification image data, that is, classification image data output from the classification model 62, is recorded when classification in the region in the classification image data is changed. The image DB 61 can have one record for one catheter image 55 captured by one rotation of the sensor 42.

In FIG. 10, the catheter image 55 is schematically shown in the XY format. Similarly, in FIG. 10, the classification image data and the non-changed classification image data are schematically shown as the classification image 51 in the XY format. The catheter image 55 in the RT format may be recorded in the image DB 61. The classification image 51 generated based on the classification image data and the non-changed classification image data may be recorded in the image DB 61.

In a first record, data corresponding to the time t1 described with reference to FIGS. 3 to 9 is recorded. Specifically, the catheter image 55 captured at the time t1 is recorded in the catheter image field. The classification image data generated by the classification model 62 is recorded in the classification image data field.

As described above, one record is recorded in the image DB 61 for one rotation of the sensor 42. In FIG. 10, for example, description from the second record to an (X1−1)-th record is omitted, and only the record corresponding to the time described with reference to FIGS. 3 to 9 is shown.

In an X1 record, data corresponding to the time t2 described with reference to FIGS. 3 to 9 is recorded. Specifically, the catheter image 55 captured at the time t2 is recorded in the catheter image field. The classification image data changed based on the classification image 51 at the time t3 is recorded in the classification image data field. The classification image data generated by the classification model 62 is recorded in the non-changed classification image data field.

In an X2 record, data corresponding to the time t3 described with reference to FIGS. 3 to 9 is recorded. Specifically, the catheter image 55 captured at the time t3 is recorded in the catheter image field. The classification image data at the time t3 is recorded in the classification image data field. Since the classification is not changed, no data is recorded in the non-changed classification image data field.

In an X3 record, data corresponding to the time t4 described with reference to FIGS. 3 to 9 is recorded. Specifically, the catheter image 55 captured at the time t4 is recorded in the catheter image field. The classification image data generated by the classification model 62 described with reference to FIG. 5 is recorded in the non-changed classification image data field. The classification image data after the second intraluminal region 512 on the lower side is changed to the first intraluminal region 511 based on the classification image data at the time t3 described with reference to FIG. 6 is recorded in the classification image data field.

In an X4 record, data corresponding to the time t5 described with reference to FIGS. 3 to 9 is recorded. Specifically, the catheter image 55 captured at the time t5 is recorded in the catheter image field. The classification image data at the time t5 is recorded in the classification image data field. Since the classification is not changed, no data is recorded in the non-changed classification image data field.

For example, when the sensor 42 is manually advanced and retracted, or when an advancing and retracting speed of the sensor 42 is variable, the image DB 61 may have a field for recording a position of the sensor 42. In accordance with an embodiment, the catheter system 10 can accurately construct a three-dimensional image using the catheter image 55 and the classification image data even when a speed at which the sensor 42 is advanced and retracted is changed.

When an angle of the catheter image 55 can be detected, the image DB 61 may have a field for recording the angle of the catheter image 55. The catheter system 10 can also accurately construct a three-dimensional image using the catheter image 55 and the classification image data even when three-dimensional scan is performed in a state where the sheath 41 is curved.

Figure 11:
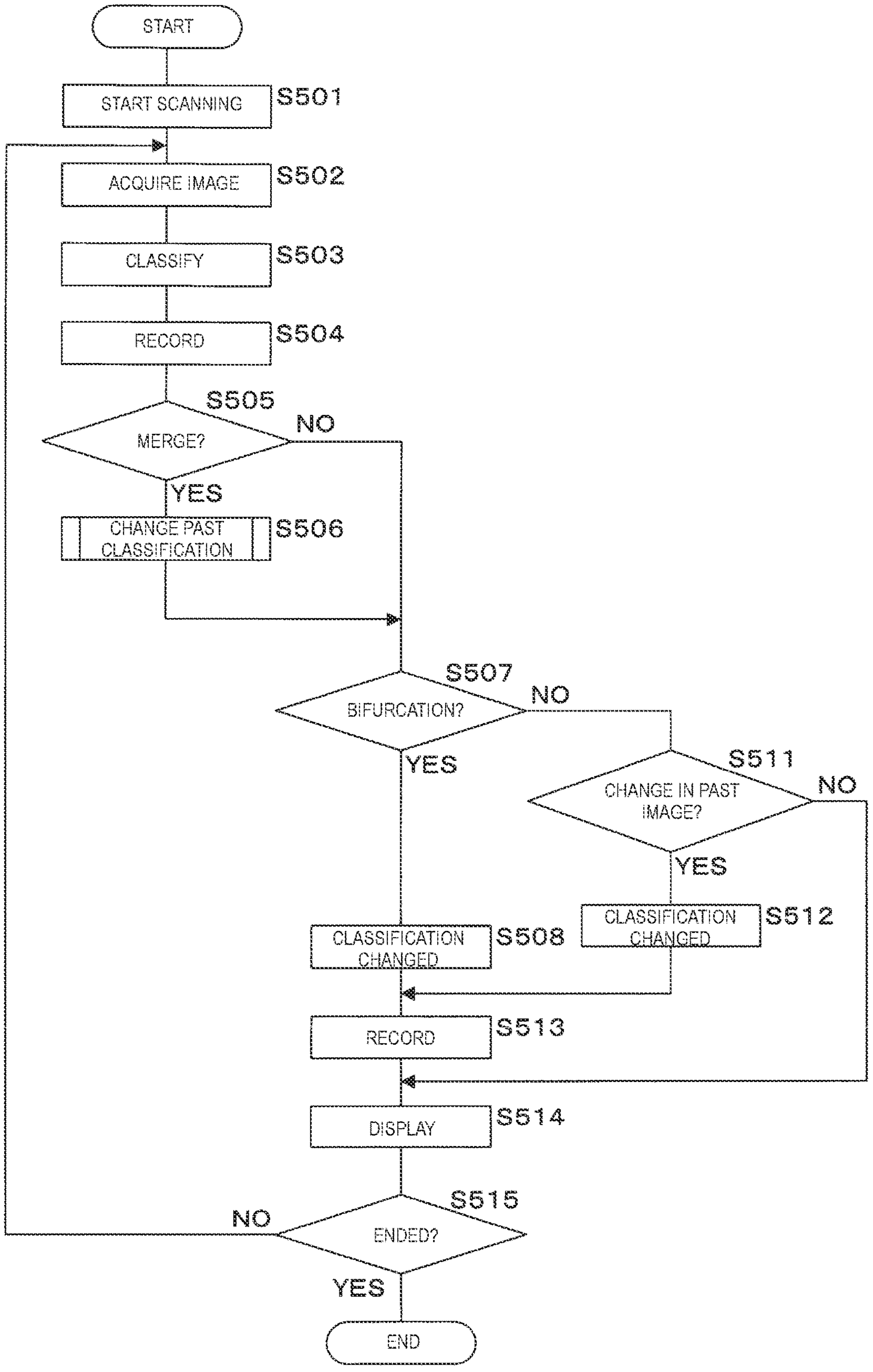
FIG. 11 is a flowchart showing a processing flow in accordance with a program.

FIG. 11 is a flowchart showing a processing flow in accordance with a program. The program in FIG. 11 is executed when a user such as a doctor instructs execution of three-dimensional scan. The control unit 21 instructs the catheter control unit 271 to start three-dimensional scan (S501). The catheter control unit 271 controls the MDU 33 to perform three-dimensional scan, and sequentially captures the catheter image 55.

The control unit 21 acquires the catheter image 55 from the catheter control unit 271 (S502). In S502, the control unit 21 implements a function of a catheter image acquisition unit of the present embodiment. The control unit 21 inputs the acquired catheter image 55 to the classification model 62 to acquire the classification image data (S503). In S503, the control unit 21 implements a function of a classification image data generation unit of the present embodiment that sequentially generates the classification image data based on the sequentially captured catheter images 55, and a function of a classification image data acquisition unit that sequentially acquires the generated classification image data.

The control unit 21 creates a new record in the image DB 61. The control unit 21 records a consecutive number in the number field. The control unit 21 records the catheter image 55 acquired in S502 in the catheter field, and records the classification image data acquired in S503 in the classification image data field (S504).

The control unit 21 determines whether the first intraluminal region 511 and the second intraluminal region 512 merge with each other (S505). Specifically, the control unit 21 compares first classification image data generated based on a first catheter image that is the latest catheter image 55 with second classification image data generated based on a second catheter image captured at a position different from the first catheter image. Here, the second catheter image is the catheter image 55 captured before the first catheter image.

When the second classification image is determined to be the second intraluminal region 512 and the first classification image includes a region determined to be the first intraluminal region 511, the control unit 21 determines that merging occurs. In S505, the control unit 21 implements a function of a merging determination unit of the present embodiment.

If it is determined that merging occurs (YES in S505), the control unit 21 activates a subroutine for changing past classification (S506). The subroutine for changing the past classification is a subroutine for changing classification of classification image data already recorded in the classification image data field of the image DB 61. A processing flow of the subroutine for changing the past classification will be described later.

If it is determined that merging does not occur (NO in S505), or after an end of S506, the control unit 21 determines whether a bifurcation from the first intraluminal region 511 to the second intraluminal region 512 occurs (S507). Specifically, the control unit 21 compares a predetermined number of classification image data from the newest recorded in the classification image data field with the latest classification image data. If there is a change in location from the first intraluminal region 511 to the second intraluminal region 512, the control unit 21 determines that a bifurcation occurs.

If it is determined that a bifurcation occurs (YES in S507), the control unit 21 generates changed classification image data in which the classification corresponding to a bifurcated portion is changed from the second intraluminal region 512 to the first intraluminal region 511 (S508).

If it is determined that there is no bifurcation (NO in S507), the control unit 21 determines whether there is a location where the second intraluminal region 512 is changed to the first intraluminal region 511 in the classification image data recorded in an immediately preceding record (S511). If it is determined that there is a changed location (YES in S511), the control unit 21 generates changed classification image data in which classification of the second intraluminal region 512 corresponding to a changed location in the immediately preceding record is changed to the first intraluminal region 511 (S512).

After S508 or S512, the control unit 21 records the changed classification image data in the image DB 61 (S513). Specifically, the control unit 21 extracts the latest record recorded in the image DB 61 and moves data recorded in the classification image data field to the non-changed classification image data field. Thereafter, the control unit 21 records the changed classification image data in the classification image data field.

If it is determined that there is no changed location (NO in S511), or after an end of S513, the control unit 21 displays a three-dimensional image based on the classification image data recorded in the classification image data field on the display unit 25 (S514). Since a method for constructing a three-dimensional image based on a plurality of classification image data is known, description thereof is omitted. In S514, the control unit 21 implements a function of a three-dimensional image output unit of the present embodiment.

The control unit 21 may transmit the three-dimensional image to the network in S514. It is possible to provide the catheter system 10 that allows the user at a remote location to check a three-dimensional image via, for example, Host Integration Server (HIS) or the like. The control unit 21 may store the three-dimensional image in S514 in the auxiliary storage device 23 or an external large-capacity storage device.

The control unit 21 determines whether the processing of the catheter image 55 acquired by one three-dimensional scan is ended (S515). If it is determined that the processing is not ended (NO in S515), the control unit 21 returns to S502. If it is determined that the processing is ended (YES in S515), the control unit 21 ends the processing.

Figure 12:
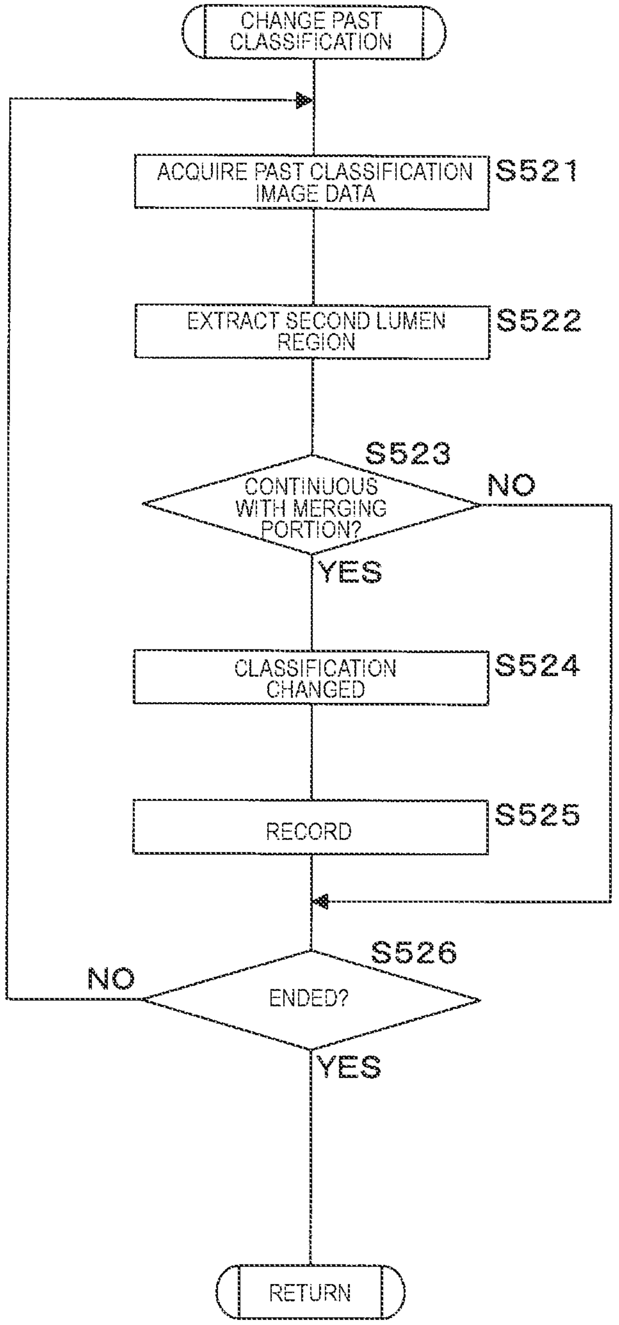
FIG. 12 is a flowchart showing a processing flow of a subroutine for changing a past classification.

FIG. 12 is a flowchart showing a processing flow of the subroutine for changing the past classification. The subroutine for changing the past classification is a subroutine for changing the classification of the classification image data already recorded in the classification image data field of the image DB 61.

The control unit 21 acquires the classification image data recorded in the past from the classification image data field of a record immediately preceding a record being processed from the image DB 61 (S521). The control unit 21 extracts a region classified as the second intraluminal region 512 from the acquired classification image data (S522).

The control unit 21 determines whether the extracted second intraluminal region 512 is continuous with a merging portion between the first intraluminal region 511 and the second intraluminal region 512 (S523). Specifically, the control unit 21 determines that the second intraluminal region 512 that is present at the same position as the second intraluminal region 512 determined to merge with the first intraluminal region 511 is continuous with the merging portion. Note that when a plurality of second intraluminal regions 512 are extracted in S522, the control unit 21 determines whether each second intraluminal region 512 is continuous with the merging portion.

If it is determined that the second intraluminal region 512 is continuous with the merging portion (YES in S523), the control unit 21 generates changed classification image data in which classification corresponding to a portion continuous with the merging portion is changed from the second intraluminal region 512 to the first intraluminal region 511 (S524). In S524, the control unit 21 implements a function of a classification change unit of the present embodiment that sequentially processes the classification image data.

The control unit 21 records the changed classification image data in the image DB 61 (S525). Specifically, the control unit 21 moves data recorded in the classification image data field of a record extracted in S521 to the non-changed classification image data field. Thereafter, the control unit 21 records the changed classification image data in the classification image data field.

When data is already recorded in the non-changed classification image data field, the control unit 21 rewrites data in the classification image data field without changing the data in the non-changed classification image data. The image DB 61 may have a field for leaving a history every time the classification image data is changed. In this way, a state in which the classification image data output from the classification model 62 is recorded as it is in the image DB 61 can be maintained.

The control unit 21 determines whether the processing is ended (S526). For example, the control unit 21 determines to end the processing if the determination of NO in S523 continues a predetermined number of times. If it is determined that the processing is not ended (NO in S526), the control unit 21 returns to S521 and performs processing of an immediately preceding record. If it is determined that the processing is ended (YES in S526), the control unit 21 ends the processing.

Figure 13:
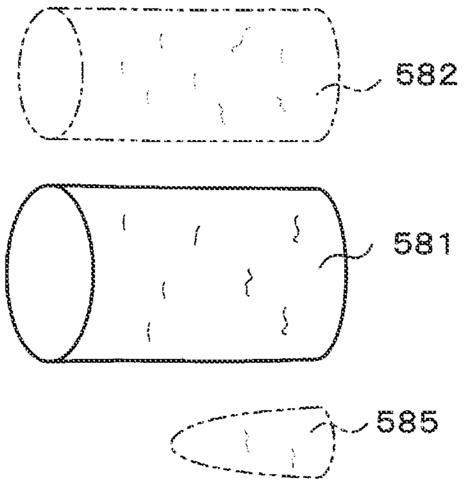
FIG. 13 is a diagram showing a display example of a three-dimensional image.
Figure 14:
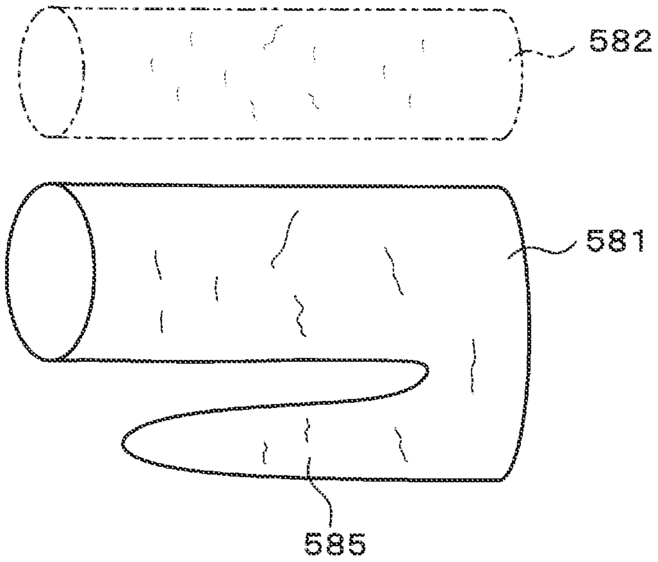
FIG. 14 is a diagram showing a display example of a three-dimensional image.
Figure 15:
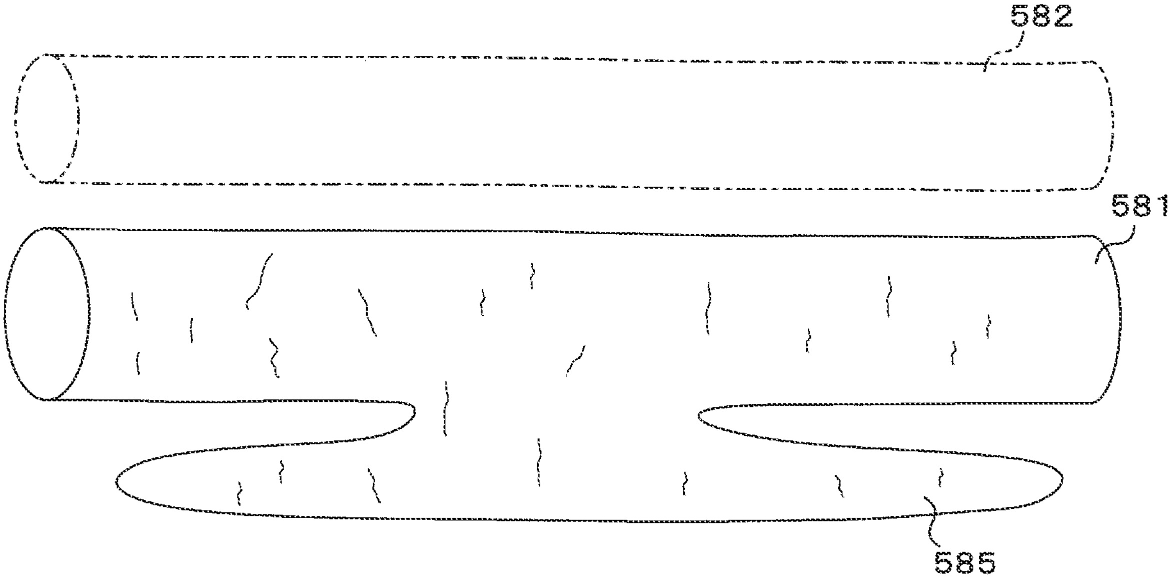
FIG. 15 is a diagram showing a display example of a three-dimensional image.

FIGS. 13 to 15 are diagrams showing display examples of a three-dimensional image. A display example of the three-dimensional image performed by the control unit 21 in S514 of FIG. 11 will be described with reference to FIGS. 13 to 15.

In the following description, a case where the user observes a shape of the first lumen 581 into which the three-dimensional image acquisition catheter 40 is inserted will be described as an example. As described above, the control unit 21 constructs a three-dimensional image based on a series of classification image data. As described above, since a method for constructing a three-dimensional image based on a series of classification image data is known, description thereof is omitted.

For example, the control unit 21 displays a portion corresponding to the first intraluminal region 511 in a non-transparent state, displays a portion corresponding to the second intraluminal region 512 in a translucent state, and does not display other portions. The shape of the first lumen 581 is represented by a portion corresponding to the first intraluminal region 511, and a shape of the second lumen 582 is represented by a portion corresponding to the second intraluminal region 512. In FIGS. 13 to 15, a non-transparent portion is indicated by a solid line, and a translucent portion is indicated by a two-dot chain line.

FIG. 13 is an example of a three-dimensional image at the time t2 described with reference to FIGS. 3 to 9. FIG. 14 is an example of a three-dimensional image at the time t3. In FIG. 13, a left end portion of the merging lumen 585 displayed in a translucent manner is changed to be non-transparent. FIG. 15 is an example of a three-dimensional image at the time t5. The first lumen 581 and the merging lumen 585 are non-transparent, and the second lumen 582 is translucent.

With the above display, the user can rather easily grasp a three-dimensional shape of a target portion in real time. Based on an instruction from the user, the control unit 21 may display the first lumen 581 in a non-transparent manner and the second lumen 582 in a translucent manner.

The control unit 21 may display the catheter image 55 in the XY format, which is a radial two-dimensional image, on the display unit 25 together with the three-dimensional image. In this case, the control unit 21 implements a function of a radial image acquisition unit that outputs the classification image 51 as a radial two-dimensional image. The control unit 21 may display the classification image 51 superimposed on the catheter image 55. In the case of performing superimposed display, the control unit 21 may display the classification image 51 in a translucent state.

The control unit 21 may display an image in a form of a linear two-dimensional image generated based on the catheter image 55 on the display unit 25. In the following description, a catheter image of a linear type may be referred to as a linear catheter image. In this case, the control unit 21 implements a function of a linear image output unit that outputs a linear catheter image. The control unit 21 may display the linear classification image 52 superimposed on the linear catheter image 55. In the case of performing superimposed display, the control unit 21 may display the linear classification image 52 in a translucent state.

For example, the control unit 21 may receive an instruction to change a position of a cross section of the linear catheter image from the user. The control unit 21 may receive an instruction to change a direction in which the three-dimensional image is displayed from the user. Since a method for appropriately changing a display format of the constructed three-dimensional image based on an instruction from the user is known, description thereof is omitted.

The control unit 21 may display a cross section obtained by cutting the constructed three-dimensional image in any plane. Since a method for receiving an instruction for a plane to cut a three-dimensional image from a user and a method for displaying a cross section based on an instruction from the user are known, description thereof is omitted.

The catheter system 10 may have a function of capturing the catheter image 55 at a fixed position without advancing and retracting the sensor 42. It is possible to provide the catheter system 10 capable of switching between a B-mode scan (i.e., a two-dimensional scan of the biological tissue), in which ultrasound is transmitted and received while the sensor 42 rotating at a fixed position, and a three-dimensional scan.

According to the present embodiment, it is possible to provide the catheter system 10 that clearly displays a structure of the merged and bifurcated lumen. Therefore, it is possible to provide the catheter system 10 that assists understanding of an image acquired by the image acquisition catheter 40.

By processing the catheter image 55 captured by the three-dimensional image acquisition catheter 40 in real time, it is possible to provide the catheter system 10 that assists, for example, an interventional radiology (IVR) procedure.

In the above description, the case where the first intraluminal region 511 has a tubular shape like a blood vessel is shown as an example, but the three-dimensional image acquisition catheter 40 may be inserted in a relatively wide place such as an atrium or a ventricle. The catheter system 10 according to the present embodiment can be used, for example, when the user observes a shape of left auricle of heart from a left atrium or a left pulmonary vein.

The control unit 21 may acquire and process the catheter image 55 recorded in advance in the auxiliary storage device 23 or an external database or the like instead of the catheter image 55 captured in real time. The control unit 21 implements the function of the catheter image acquisition unit.

The control unit 21 may acquire and process classification image data recorded in advance in the auxiliary storage device 23 or an external database or the like. The control unit 21 implements the function of the classification image data acquisition unit that acquires a plurality of classification image data. In such a case, the information processing device 20 may be an information processing device, for example, such as a general-purpose personal computer, a smartphone, or a tablet that does not include the catheter control unit 271.

Second Embodiment

The present embodiment relates to the catheter system 10 that records a region of the second intraluminal region 512 determined to merge with the first intraluminal region 511. Description of parts common to the first embodiment is omitted.

Figure 16:
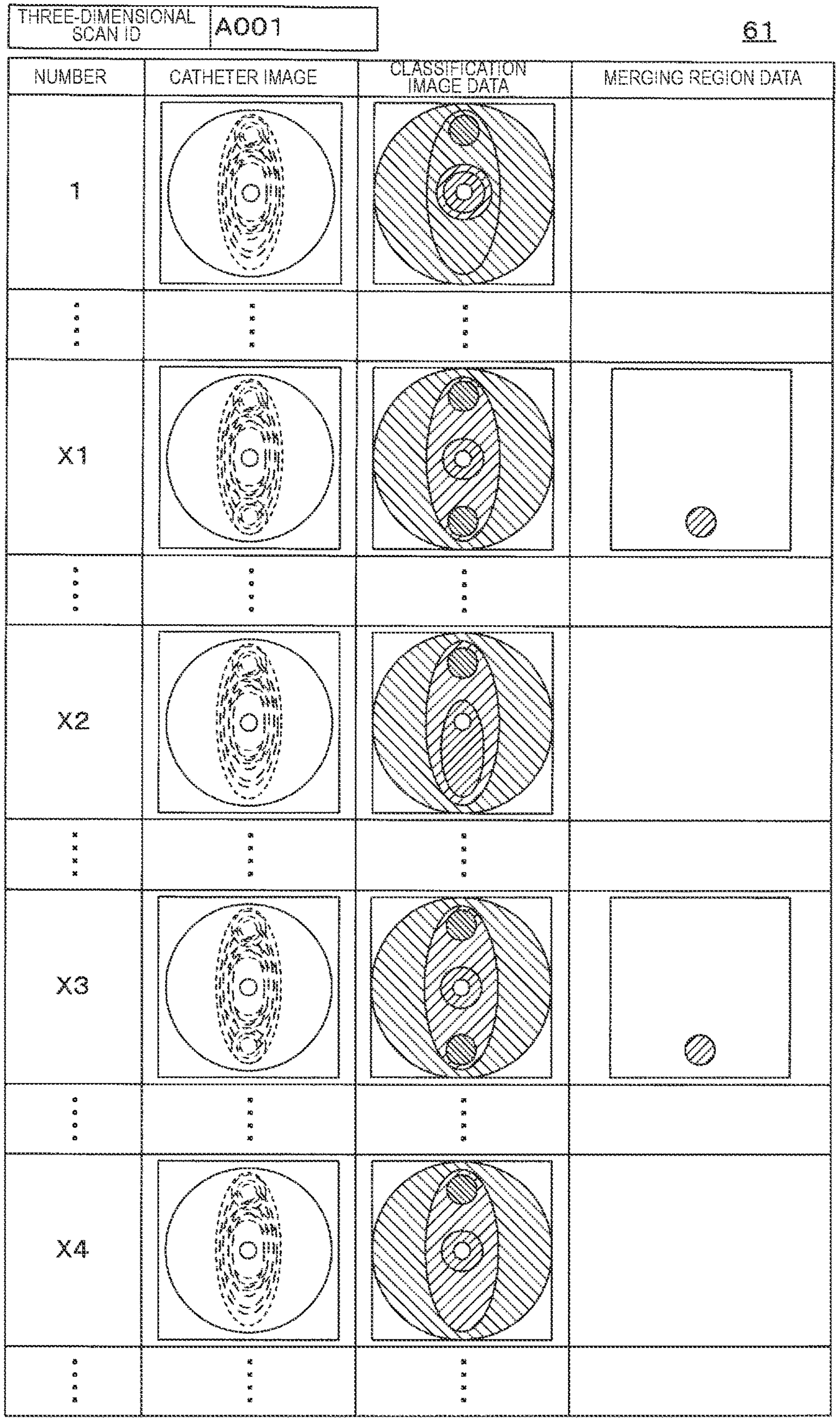
FIG. 16 is a diagram showing a record layout of the image DB according to a second embodiment.

FIG. 16 is a diagram showing a record layout of the image DB 61 according to a second embodiment. The image DB 61 is a database (DB) that records the catheter image 55, the classification image data, and the merging region data in association with one another. The image DB 61 can include a three-dimensional scan ID field, a number field, a catheter image field, a classification image data field, and a merging region data field.

In the three-dimensional scan ID field, a three-dimensional scan ID uniquely assigned to each three-dimensional scan is recorded. In the number field, a number indicating a capturing order is recorded as a consecutive number in each catheter image 55 captured by one three-dimensional scan. In the catheter image field, a file in which the catheter image 55 is recorded or a location of the file in which the catheter image 55 is recorded is recorded.

In the classification image data field, a file in which the classification image data is recorded or a location of the file in which the classification image data is recorded is recorded. In the present embodiment, the classification image data recorded in the classification image data field is the classification image data output from the classification model 62.

In the merging region data field, a file in which merging region data is recorded or a location of the file in which the merging region data is recorded is recorded. The merging region data is data in which only a region that is the second intraluminal region 512 in the classification image data output from the classification model 62 and that is determined to merge with the first intraluminal region 511 as described in the first embodiment is recorded.

In FIG. 16, the merging region data is schematically shown in the XY format. The merging region data can be, for example, data in which "1" is associated with a pixel in a region determined to merge and "0" is associated with a pixel determined not to merge. The merging region data may be data in which only a label associated with a region of the classification image data that is determined to merge with the first intraluminal region 511 is retained, and labels associated with other regions are changed to "0", for example.

In a first record, data corresponding to the time t1 described with reference to FIGS. 3 to 9 is recorded. Specifically, the catheter image 55 captured at the time t1 is recorded in the catheter image field. The classification image data generated by the classification model 62 is recorded in the classification image data field. No data is recorded in the merging region data field.

In an X1 record, data corresponding to the time t2 described with reference to FIGS. 3 to 9 is recorded. Specifically, the catheter image 55 captured at the time t2 is recorded in the catheter image field. The classification image data generated by the classification model 62 is recorded in the classification image data field. Data indicating only a region of the second intraluminal region 512 determined to merge with the first intraluminal region 511 based on the classification image 51 at the time t3 is recorded in the merging region data field.

In an X2 record, data corresponding to the time t3 described with reference to FIGS. 3 to 9 is recorded. Specifically, the catheter image 55 captured at the time t3 is recorded in the catheter image field. The classification image data at the time t3 is recorded in the classification image data field. Since there is no region determined to merge, no data is recorded in the merging region data field.

In an X3 record, data corresponding to the time t4 described with reference to FIGS. 3 to 9 is recorded. Specifically, the catheter image 55 captured at the time t4 is recorded in the catheter image field. The classification image data generated by the classification model 62 is recorded in the classification image data field. Data indicating only a region of the second intraluminal region 512 determined to merge with the first intraluminal region 511 based on the classification image 51 at the time t3 is recorded in the merging region data field.

In an X4 record, data corresponding to the time t5 described with reference to FIGS. 3 to 9 is recorded. Specifically, the catheter image 55 captured at the time t5 is recorded in the catheter image field. The classification image data at the time t5 is recorded in the classification image data field. Since there is no region determined to merge, no data is recorded in the merging region data field.

Figure 17:
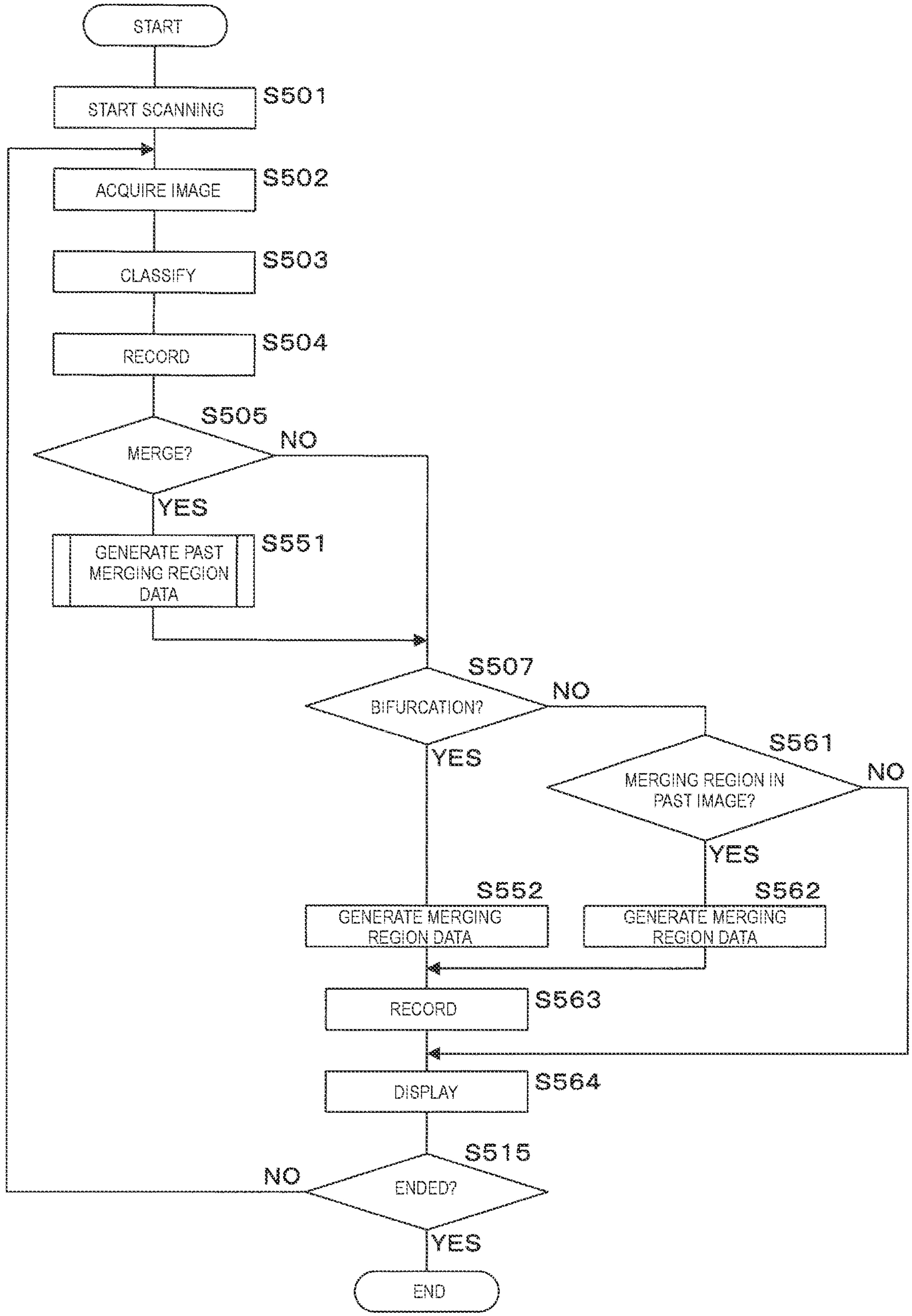
FIG. 17 is a flowchart showing a processing flow in accordance with a program according to the second embodiment.

FIG. 17 is a flowchart showing a processing flow in accordance with a program according to the second embodiment. The program for FIG. 17 is executed instead of the program according to the first embodiment described with reference to FIG. 11. Since the processing from S501 to S505 is the same as the processing flow in accordance with the program described with reference to FIG. 11, description of S501 to S505 is omitted.

If it is determined that merging occurs (YES in S505), the control unit 21 activates a subroutine for generating past merging region data (S551). The subroutine for generating the past merging region data is a subroutine for generating merging region data corresponding to a portion of the second intraluminal region 512 that merges with the first intraluminal region 511 based on classification image data already recorded in the classification image data field of the image DB 61. A processing flow of the subroutine for generating the past merging region data will be described later.

If it is determined that merging does not occur (NO in S505), or after an end of S551, the control unit 21 determines whether a bifurcation from the first intraluminal region 511 to the second intraluminal region 512 occurs (S507). If it is determined that a bifurcation occurs (YES in S507), the control unit 21 extracts the second intraluminal region 512 corresponding to a bifurcated portion and generates merging region data (S552).

If it is determined that there is no bifurcation (NO in S507), the control unit 21 determines whether the merging region data is recorded in a merging region data field of an immediately preceding record (S561). If it is determined that the merging region data is recorded (YES in S561), the control unit 21 extracts the second intraluminal region 512 corresponding to merging region data in the immediately preceding record and generates merging region data (S562).

After completing S552 or S562, the control unit 21 records the merging region data in the image DB 61 (S563). Specifically, the control unit 21 extracts the latest record recorded in the image DB 61 and records the merging region data in a changed region data field.

If it is determined that the merging region data is not recorded (NO in S561), or after completing S563, the control unit 21 displays a three-dimensional image based on the classification image data recorded in the classification image data field and the merging region data field on the display unit 25 (S564). A display example of the three-dimensional image will be described later.

The control unit 21 determines whether the processing of the catheter image 55 acquired by one three-dimensional scan is ended (S515). If it is determined that the processing is not ended (NO in S515), the control unit 21 returns to S502. If it is determined that the processing is ended (YES in S515), the control unit 21 ends the processing.

Figure 18:
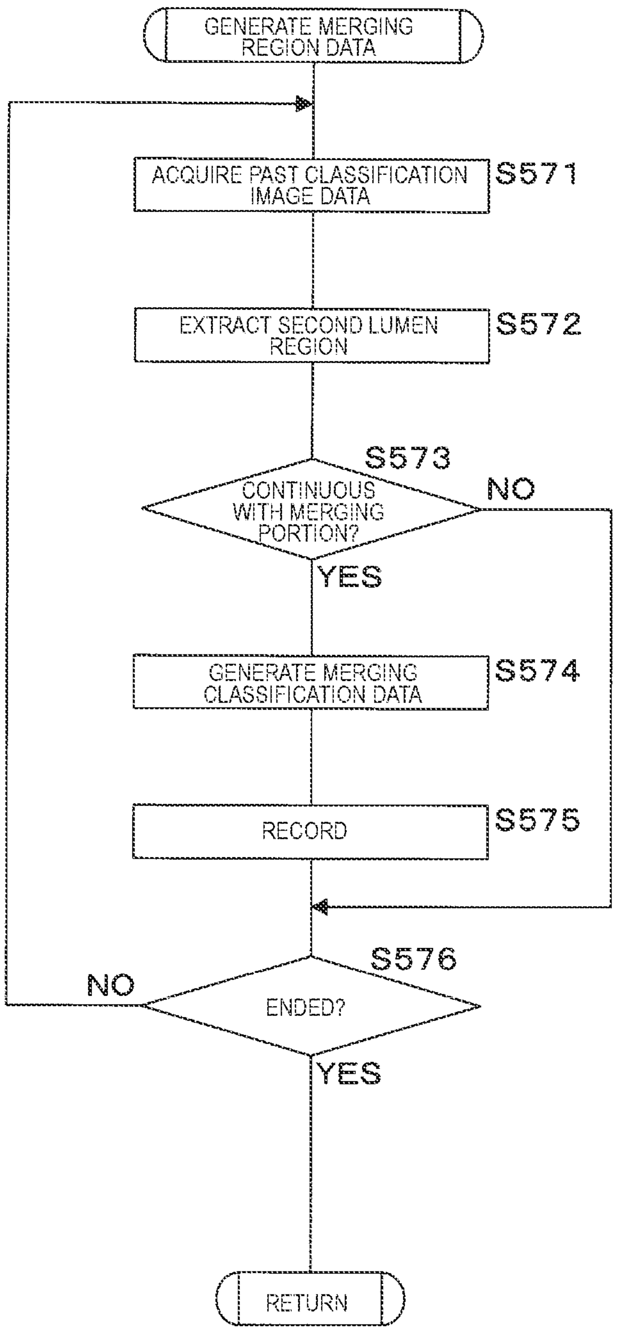
FIG. 18 is a flowchart showing a processing flow of a subroutine for generating past merging region data.

FIG. 18 is a flowchart showing a processing flow of a subroutine for generating past merging region data. The subroutine for generating the past merging region data is a subroutine for generating merging region data corresponding to a portion of the second intraluminal region 512 that merges with the first intraluminal region 511 based on classification image data already recorded in the classification image data field of the image DB 61.

The control unit 21 acquires the classification image data recorded in the past from the classification image data field of a record immediately preceding a record being processed from the image DB 61 (S571). The control unit 21 extracts a region classified as the second intraluminal region 512 from the acquired classification image data (S572).

The control unit 21 determines whether the extracted second intraluminal region 512 is continuous with a merging portion between the first intraluminal region 511 and the second intraluminal region 512 (S573). If it is determined that the second intraluminal region 512 is continuous with the merging portion (YES in S573), the control unit 21 extracts the second intraluminal region 512 corresponding to a portion continuous with the merging portion and generates merging region data (S574).

The control unit 21 records the merging region data in the image DB 61 (S525). Specifically, the control unit 21 records merging classification data generated in S574 in the merging region data field of a record extracted in S571.

The control unit 21 determines whether the processing is ended (S576). For example, the control unit 21 determines to end the processing if the determination of NO in S573 continues a predetermined number of times. If it is determined that the processing is not ended (NO in S576), the control unit 21 returns to S571 and performs processing of an immediately preceding record. If it is determined that the processing is ended (YES in S576), the control unit 21 ends the processing.

Figure 19:
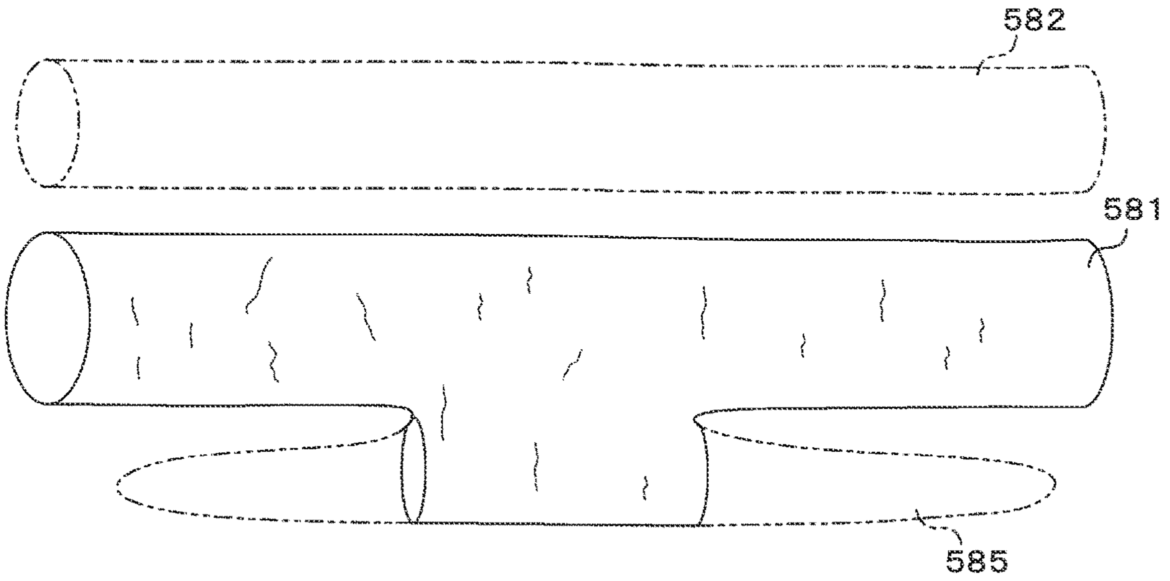
FIG. 19 is a diagram showing a screen example according to the second embodiment.
Figure 20:
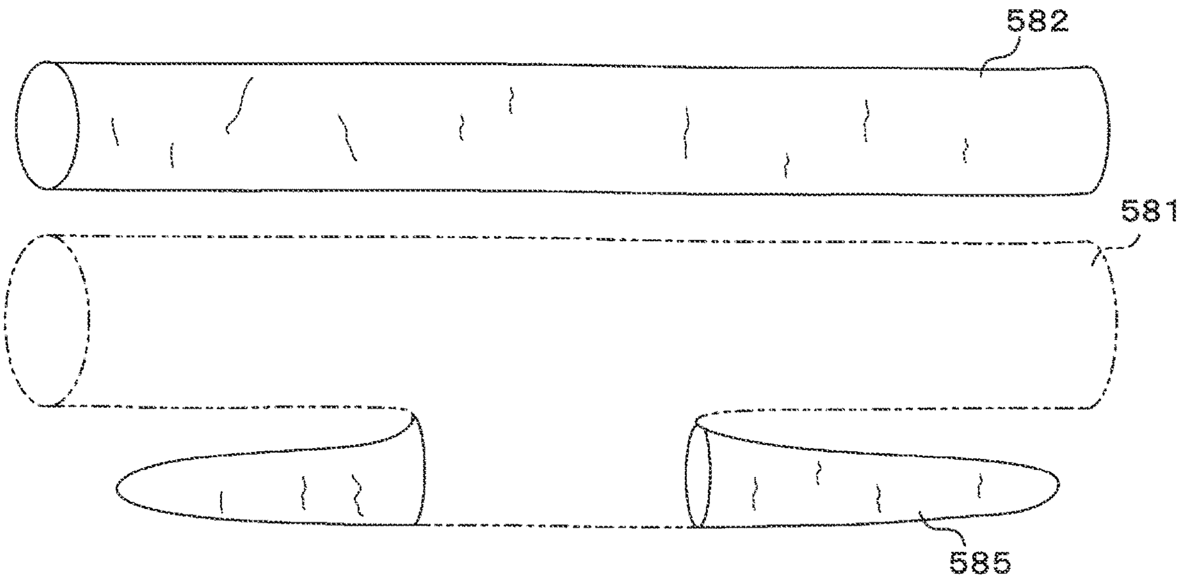
FIG. 20 is a diagram showing a screen example according to the second embodiment.
Figure 21:
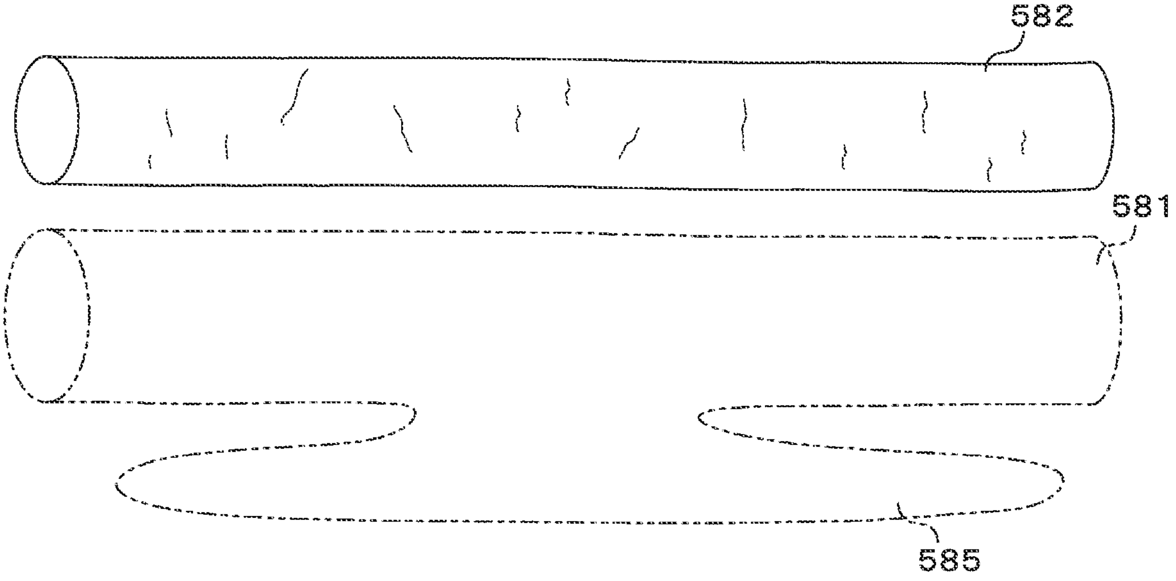
FIG. 21 is a diagram showing a screen example according to the second embodiment.

FIGS. 19 to 21 are diagrams showing screen examples according to the second embodiment. FIGS. 19 to 21 are examples of the three-dimensional image at the time t5 described with reference to FIGS. 3 to 9. FIG. 19 shows an example of displaying a three-dimensional image constructed based on a series of classification image data recorded in the classification image data field.

In FIG. 19, the control unit 21 displays a portion corresponding to the first intraluminal region 511 in a non-transparent state, displays a portion corresponding to the second intraluminal region 512 in a translucent state, and does not display other portions. As described with reference to FIG. 16, both end portions of the merging lumen 585 are shown in a translucent manner, as is the second intraluminal region 512.

The control unit 21 may receive an instruction to display only a portion of the second intraluminal region 512 corresponding to the merging region data in the same manner as the first intraluminal region 511. When such an instruction is received, the control unit 21 displays a portion corresponding to the merging region data in the same manner as the first intraluminal region 511. That is, as described with reference to FIG. 15, the control unit 21 displays the first lumen 581 and the merging lumen 585 in a non-transparent manner and displays the second lumen 582 in a translucent manner.

The control unit 21 may receive an instruction to display a region corresponding to the merging region data in a manner different from the first lumen 581 and the second lumen 582. For example, the control unit 21 may display both the end portions of the merging lumen 585 shown in FIG. 19 with a transparency intermediate between the first intraluminal region 511 and the second intraluminal region 512.

In FIG. 20, the control unit 21 displays a portion corresponding to the first intraluminal region 511 in a translucent state, displays a portion corresponding to the second intraluminal region 512 in a non-transparent state, and does not display other portions. For example, when an instruction to display only the second intraluminal region 512 including a portion that merges with the first intraluminal region 511 in a non-transparent state is received from the user, the control unit 21 performs the display shown in FIG. 20.

In FIG. 21, the control unit 21 displays a portion of the first intraluminal region 511 and the second intraluminal region 512 that merges with the first intraluminal region 511 in a translucent state, displays a portion corresponding to the other second intraluminal regions 512 in a non-transparent state, and does not display other portions. For example, when an instruction to display only the second intraluminal region 512 that does not merge with the first intraluminal region 511 in a non-transparent state is received from the user, the control unit 21 performs the display shown in FIG. 21.

According to the present embodiment, by recording both the classification image data and the merging region data in the image DB 61, it is possible to provide the catheter system 10 in which various displays according to an instruction from the user are displayed.

Third Embodiment

Figure 22:
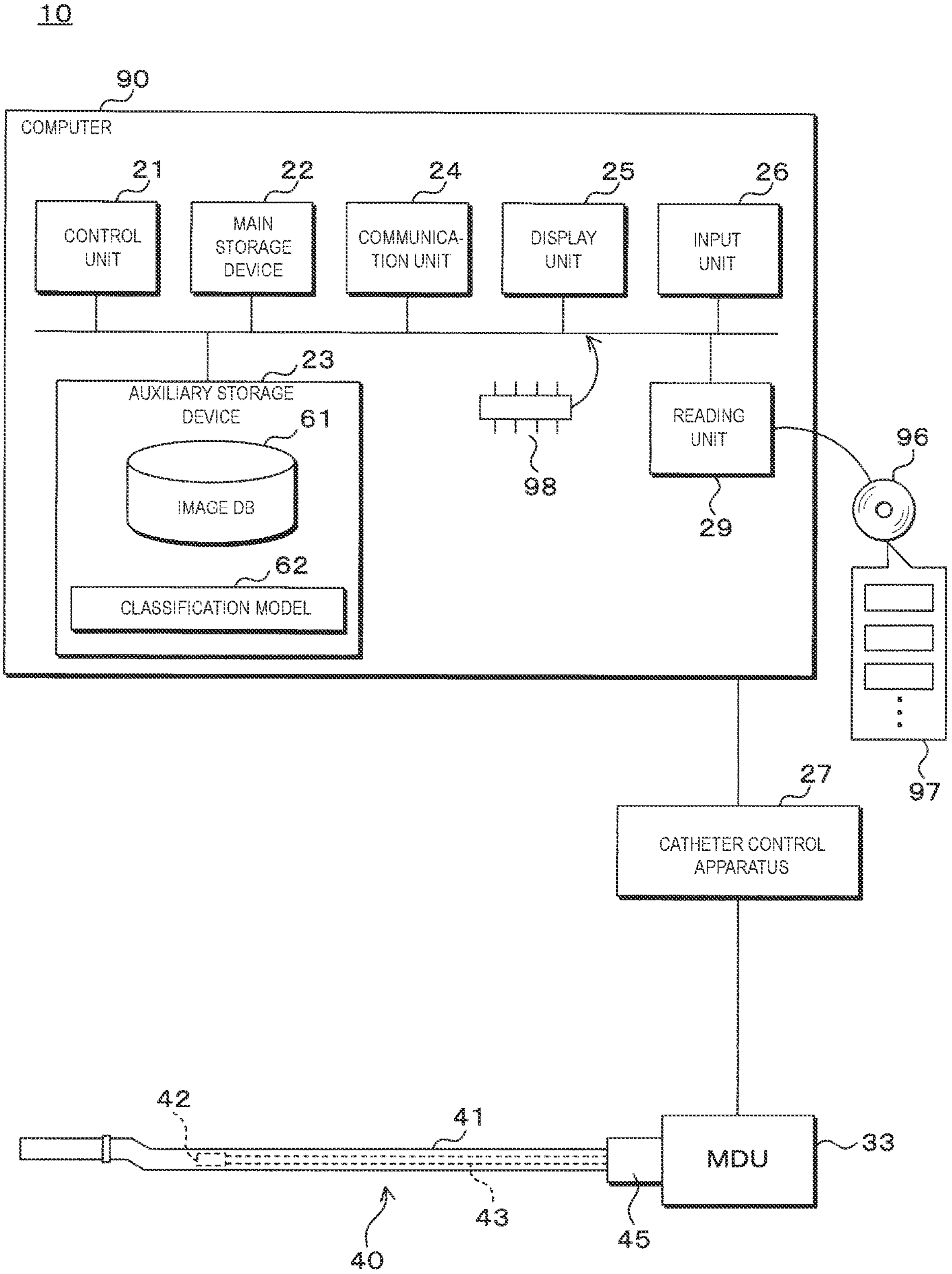
FIG. 22 is a diagram showing a configuration of a catheter system according to a third embodiment.

FIG. 22 is a diagram showing a configuration of the catheter system 10 according to a third embodiment. The present embodiment relates to a form of implementing the catheter system 10 of the present embodiment by operating a catheter control apparatus 27, the MDU 33, the three-dimensional image acquisition catheter 40, a general-purpose computer 90, and a program 97 in combination. Description of parts common to the first embodiment is omitted.

The catheter control apparatus 27 is an ultrasound diagnostic apparatus for intravascular ultrasound (IVUS) that executes control over the MDU 33, control over the sensor 42, and generation of a transverse tomographic image and a longitudinal tomographic image based on a signal received from the sensor 42. Since a function and configuration of the catheter control apparatus 27 are similar as those of an ultrasound diagnostic apparatus used in the related art, description thereof is omitted.

The catheter system 10 according to the present embodiment includes the computer 90. The computer 90 can include the control unit 21, the main storage device 22, the auxiliary storage device 23, the communication unit 24, the display unit 25, the input unit 26, a reading unit 29, and a bus. The computer 90 can be, for example, an information apparatus such as a general-purpose personal computer, a tablet, a smartphone, or a server computer. The computer 90 may be, for example, a large computing center (i.e., supercomputer), a virtual machine operating on a large computing center (i.e., supercomputer), a cloud computing system, a quantum computer, or a plurality of personal computers performing distributed processing.

The program 97 is recorded in a portable recording medium 96. The control unit 21 reads the program 97 via the reading unit 29 and stores the program 97 in the auxiliary storage device 23. The control unit 21 may read the program 97 stored in a semiconductor memory 98 such as a flash memory installed in the computer 90. Further, the control unit 21 may download the program 97 from another server computer connected via the communication unit 24 and the network and store the program 97 in the auxiliary storage device 23.

The program 97 is installed as a control program of the computer 90, is loaded into the main storage device 22, and is executed. Accordingly, the computer 90 and the catheter control apparatus 27 cooperate with each other to function as the above-described information processing device 20.

Fourth Embodiment

Figure 23:
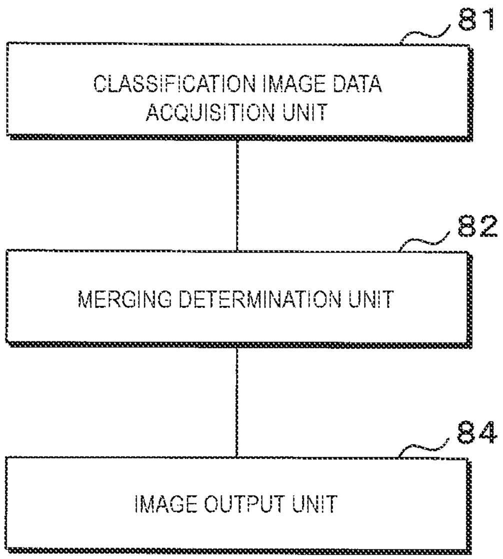
FIG. 23 is a functional block diagram of an information processing device according to a fourth embodiment.

FIG. 23 is a functional block diagram of the information processing device 20 according to a fourth embodiment. The information processing device 20 can include a classification image data acquisition unit 81, a merging determination unit 82, and an image output unit 84. The classification image data acquisition unit 81 acquires a plurality of classification image data classified into a plurality of regions including the first intraluminal region 511 into which the image acquisition catheter 40 that acquires an image while moving in the axial direction is inserted and the second intraluminal region 512 into which the image acquisition catheter 40 is not inserted, based on a plurality of catheter images 55 acquired using the image acquisition catheter 40.

The merging determination unit 82 determines whether the second intraluminal region 512 in the first catheter image of the plurality of catheter images merges with the first intraluminal region 511 in the second catheter image acquired at an axial position different from an axial position of the first catheter image.

The image output unit 84 outputs an image including the first intraluminal region 511 based on the plurality of classification image data. The image output unit 84 outputs, of the second intraluminal regions 512, only the second intraluminal region 512 in the first catheter image that is determined to merge by the merging determination unit 82, together with the first intraluminal region 511 as a region image.

Fifth Embodiment

Figure 24:
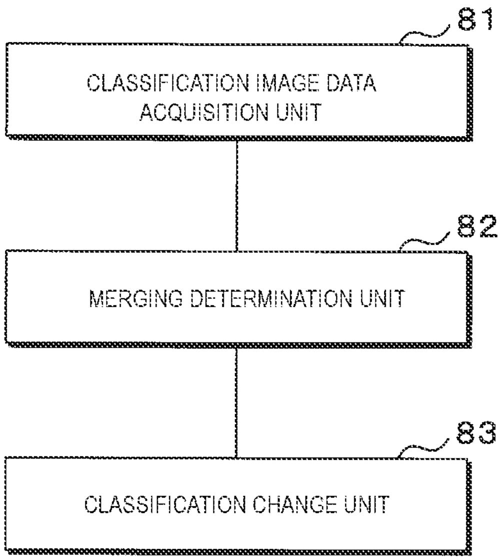
FIG. 24 is a functional block diagram of an information processing device according to a fifth embodiment.

FIG. 24 is a functional block diagram of the information processing device 20 according to a fifth embodiment. The information processing device 20 includes the classification image data acquisition unit 81, the merging determination unit 82, and a classification change unit 83. The classification image data acquisition unit 81 acquires a plurality of classification image data in which each of a plurality of catheter images 55 acquired using the image acquisition catheter 40 is classified into a plurality of regions including the first intraluminal region 511 into which the image acquisition catheter 40 is inserted and the second intraluminal region 512 into which the image acquisition catheter 40 is not inserted.

The merging determination unit 82 determines whether the second intraluminal region 512 in the first catheter image of the plurality of catheter images 55 merges with the first intraluminal region 511 in the second catheter image acquired at a time different from the first catheter image. When the merging determination unit 82 determines that merging occurs, the classification change unit 83 changes classification of the second intraluminal region 512 in the first catheter image to the first intraluminal region 511.

Technical features (configuration requirements) described in each embodiment can be combined with one another to form new technical features.

The detailed description above describes embodiments of an information processing device, an information processing method, and a program. The invention is not limited, however, to the precise embodiments and variations described. Various changes, modifications and equivalents may occur to one skilled in the art without departing from the spirit and scope of the invention as defined in the accompanying claims. It is expressly intended that all such changes, modifications and equivalents which fall within the scope of the claims are embraced by the claims.

What is claimed is:

1. An information processing device comprising:

a classification image data acquisition unit configured to acquire a plurality of items of classification image data, the plurality of items of classification image data being generated based on a plurality of catheter images acquired using an image acquisition catheter that acquires an image while moving in an axial direction on a scan plane, the plurality of items of classification image data being classified into a plurality of regions including a first intraluminal region into which the image acquisition catheter is inserted and a second intraluminal region into which the image acquisition catheter is not inserted;

a merging determination unit configured to determine whether the second intraluminal region in a first catheter image of the plurality of catheter images merges with the first intraluminal region in a second catheter image acquired at an axial position different from an axial position of the first catheter image;

an image output unit configured to output a region image including the first intraluminal region based on the plurality of items of classification image data; and a control unit configured to implement the classification image data acquisition unit, the merging determination unit, and the image output unit, the control unit is configured to extract a region classified as the second intraluminal region from the acquired classification image data;

wherein the control unit is configured to determine whether the extracted second intraluminal region is continuous with a merging portion between the first intraluminal region and the second intraluminal region, and wherein (1) the control unit is configured to implement a classification change unit configured to change classification of the second intraluminal region in the first catheter image of the classification image data that is determined to merge by the merging determination unit to the first intraluminal region, wherein the image output unit is configured to output, of the second intraluminal region acquired by the classification image data acquisition unit, only the second intraluminal region whose classification is changed by the classification change unit together with the first intraluminal region as the region image, or (2) the control unit is configured to extract the second intraluminal region corresponding to a portion continuous with the merging portion and to generate a merging region data, and the image output unit is configured to display only a portion of the second intraluminal region corresponding to the merging region data in the same manner as the first intraluminal region or to display a region corresponding to the merging region data in a manner different from the first lumen and the second lumen.

2. The information processing device according to claim 1, wherein the image output unit includes a three-dimensional image output unit configured to output a three-dimensional image including the first intraluminal region as the region image based on the plurality of items of classification image data.

3. The information processing device according to claim 1, wherein the image acquisition catheter is a radial scan catheter;

the information processing device further comprises a radial image output unit configured to output one of the plurality of catheter images as a radial two-dimensional image; and the image output unit is configured to output the region image generated based on the catheter images so as to be superimposed on the radial two-dimensional image.

4. The information processing device according to claim 1, wherein the image acquisition catheter is a radial scan catheter;

a linear image output unit configured to output a linear two-dimensional image along the axial direction; and the image output unit is configured to output the region image so as to be superimposed on the linear two-dimensional image.

5. The information processing device according to claim 1, further comprising:

a catheter image acquisition unit configured to acquire the plurality of catheter images; and a classification image data generation unit configured to classify the plurality of catheter images into a plurality of regions including the first intraluminal region and the second intraluminal region and to generate the classification image data.

6. The information processing device according to claim 5, wherein the classification image data generation unit is configured to input, when receiving a catheter image, the acquired catheter image into a trained model that outputs classification image data obtained by classifying each region of the catheter image into a predetermined region, and generate the classification image data based on the acquired catheter image.

7. The information processing device according to claim 5, wherein the catheter image acquisition unit is configured to sequentially acquire catheter images acquired using the image acquisition catheter in real time; and the classification image data generation unit is configured to sequentially generate the classification image data.

8. The information processing device according to claim 7, wherein the classification change unit is configured to sequentially process the classification image data generated by the classification image data generation unit.

9. The information processing device according to claim 1, wherein the classification image data is classified into the first intraluminal region, the second intraluminal region, a biological tissue region, and a non-intraluminal region that is none of the aforementioned regions.

10. An information processing method executed by a computer, the information processing method comprising:

acquiring a plurality of items of classification image data, the plurality of items of classification image data being generated based on a plurality of catheter images acquired using an image acquisition catheter that acquires an image while moving in an axial direction on a scan plane, the plurality of items of classification image data being classified into a plurality of regions including a first intraluminal region into which the image acquisition catheter is inserted and a second intraluminal region into which the image acquisition catheter is not inserted;

determining whether the second intraluminal region in a first catheter image of the plurality of catheter images merges with the first intraluminal region in a second catheter image acquired at an axial position different from an axial position of the first catheter image;

extracting a region classified as the second intraluminal region from the acquired classification image date;

determining whether the extracted second intraluminal region is continuous with a merging portion between the first intraluminal region and the second intraluminal region; and (1) changing classification of the second intraluminal region in the first catheter image of the classification image data that is determined to merge by the merging determination unit to the first intraluminal region, outputting of the second intraluminal region acquired by the classification image data acquisition unit, only the second intraluminal region whose classification is changed by the classification change unit together with the first intraluminal region as the region image, or (2) extracting the second intraluminal region corresponding to a portion continuous with the merging portion and to generate a merging region data, displaying only a portion of the second intraluminal region corresponding to the merging region data in the same manner as the first intraluminal region or displaying a region corresponding to the merging region data in a manner different from the first lumen and the second lumen.

11. The information processing method according to claim 10, further comprising:

outputting a three-dimensional image including the first intraluminal region as the region image based on the plurality of items of classification image data.

12. The information processing method according to claim 10, wherein the image acquisition catheter is a radial scan catheter, the method further comprises:

outputting one of the plurality of catheter images as a radial two-dimensional image; and outputting the region image generated based on the plurality of catheter images so as to be superimposed on the radial two-dimensional image.

13. The information processing method according to claim 10, wherein the image acquisition catheter is a radial scan catheter, the method further comprises:

outputting a linear two-dimensional image along the axial direction; and outputting the region image so as to be superimposed on the linear two-dimensional image.

14. The information processing method according to claim 10, further comprising:

acquiring the plurality of catheter images; and classifying the catheter images into a plurality of regions including the first intraluminal region and the second intraluminal region and to generate the classification image data.

15. The information processing method according to claim 14, further comprising:

inputting, when receiving a catheter image, the acquired catheter image into a trained model and outputting classification image data obtained by classifying each region of the catheter image into a predetermined region, and generating the classification image data based on the acquired catheter image.

16. The information processing method according to claim 14, further comprising:

sequentially acquiring catheter images acquired using the image acquisition catheter in real time;

sequentially generating the classification image data; and sequentially processing the generated classification image data.

17. The information processing method according to claim 10, wherein the classification image data is classified into the first intraluminal region, the second intraluminal region, a biological tissue region, and a non-intraluminal region that is none of the aforementioned regions.

18. A non-transitory computer-readable medium storing a program causing a computer to execute a process comprising:

acquiring a plurality of items of classification image data, the plurality of items of classification image data being generated based on a plurality of catheter images acquired using an image acquisition catheter that acquires an image while moving in an axial direction on a scan plane, the plurality of items of classification image data being classified into a plurality of regions including a first intraluminal region into which the image acquisition catheter is inserted and a second intraluminal region into which the image acquisition catheter is not inserted;

determining whether the second intraluminal region in a first catheter image of the plurality of catheter images merges with the first intraluminal region in a second catheter image acquired at an axial position different from an axial position of the first catheter image;

extracting a region classified as the second intraluminal region from the acquired classification image date;

determining whether the extracted second intraluminal region is continuous with a merging portion between the first intraluminal region and the second intraluminal region; and (1) changing classification of the second intraluminal region in the first catheter image of the classification image data that is determined to merge by the merging determination unit to the first intraluminal region, outputting of the second intraluminal region acquired by the classification image data acquisition unit, only the second intraluminal region whose classification is changed by the classification change unit together with the first intraluminal region as the region image, or (2) extracting the second intraluminal region corresponding to a portion continuous with the merging portion and to generate a merging region data, displaying only a portion of the second intraluminal region corresponding to the merging region data in the same manner as the first intraluminal region or displaying a region corresponding to the merging region data in a manner different from the first lumen and the second lumen.

* * * * *